United States Patent
Takii et al.

(10) Patent No.: US 10,537,239 B2
(45) Date of Patent: Jan. 21, 2020

(54) SUBJECTIVE OPTOMETRY APPARATUS

(71) Applicant: NIDEK CO., LTD., Gamagori, Aichi (JP)

(72) Inventors: Michihiro Takii, Aichi (JP); Masaaki Hanebuchi, Aichi (JP); Hisashi Ochi, Aichi (JP); Sasagu Tachibana, Aichi (JP)

(73) Assignee: NIDEK CO., LTD., Gamagori, Aichi (JP)

( * ) Notice: Subject to any disclaimer, the term of this patent is extended or adjusted under 35 U.S.C. 154(b) by 164 days.

(21) Appl. No.: 15/913,029

(22) Filed: Mar. 6, 2018

(65) Prior Publication Data

US 2018/0256022 A1     Sep. 13, 2018

(30) Foreign Application Priority Data

Mar. 7, 2017  (JP) ................................. 2017-042454
Mar. 7, 2017  (JP) ................................. 2017-042455

(51) Int. Cl.
*A61B 3/00*   (2006.01)
*A61B 3/028*  (2006.01)
*A61B 3/103*  (2006.01)
*A61B 3/15*   (2006.01)

(52) U.S. Cl.
CPC .......... *A61B 3/0008* (2013.01); *A61B 3/0091* (2013.01); *A61B 3/028* (2013.01); *A61B 3/103* (2013.01); *A61B 3/152* (2013.01); *A61B 2560/0223* (2013.01)

(58) Field of Classification Search
CPC ..... A61B 3/0008; A61B 3/0091; A61B 3/028; A61B 3/103; A61B 3/152; A61B 2560/0223
See application file for complete search history.

(56) References Cited

U.S. PATENT DOCUMENTS

2014/0211165 A1*  7/2014  Kobayashi ............. A61B 3/032
                                                351/237

FOREIGN PATENT DOCUMENTS

JP           5-176893 A        7/1993

* cited by examiner

*Primary Examiner* — Wen Huang
(74) *Attorney, Agent, or Firm* — Sughrue Mion, PLLC

(57) ABSTRACT

A subjective optometry apparatus includes a light projecting optical system that projects a target light flux to an examinee's eye, a fixed optical element that guides an image of the target light flux to the examinee's eye so as to have an optically predetermined examination length, a calibration optical system disposed in an optical path of the light projecting optical system to change optical characteristics of the examinee's eye, a measurement unit that accommodates the light projecting optical system; a positional information acquiring portion that acquires positional information of the measurement unit, a correction amount setting portion that sets a correction amount for correcting a projection magnification of the target light flux projected to the examinee's eye, based on the positional information, and a correction portion that corrects the projection magnification of the target light flux based on the correction amount set by the correction amount setting portion.

9 Claims, 12 Drawing Sheets

SUBJECTIVE OPTOMETRY APPARATUS

CROSS-REFERENCE TO RELATED APPLICATION

This application claims priority from Japanese Patent Application No. 2017-042454 filed on Mar. 7, 2017 and Japanese Patent Application No. 2017-042455 filed on Mar. 7, 2017, the entire subject-matter of which is incorporated herein by reference.

TECHNICAL FIELD

This disclosure relates to a subjective optometry apparatus for measuring optical characteristics of an examinee's eye.

BACKGROUND

There has been known a subjective optometry apparatus that measures optical characteristics (refractive power or the like) of an examinee's eye by disposing an optical elements such as a spherical lens or a cylindrical lens in front of the examinee's eye and presenting an examination target to the examinee's eye via the optical elements (for example, see JP-A-H05-176893). When the optical characteristics of the examinee's eye are measured, the position adjustment (alignment) of the examinee's eye and the subjective optometry apparatus is performed.

In a subjective examination, a different examination target depending on a visual acuity value of an examinee's eye is presented to the examinee's eye such that every examination target has a constant size, by the position adjustment (alignment) of the examinee's eye and the subjective optometry apparatus. For example, the inventors study a subjective optometry apparatus, as an example, which includes a light projecting optical system that projects a target light flux to an examinee's eye and a fixed optical element that guides the target light flux from the light projecting optical system to the examinee's eye so as to have an optically predetermined examination length, performs the position adjustment with respect to the examinee's eye by moving a measurement unit accommodating the light projecting optical system, and projects, via the fixed optical element to the examinee's eye, the target light flux from the light projecting optical system of the position-adjusted measurement unit.

Incidentally, in such a subjective optometry apparatus, especially, in a subjective optometry apparatus in which a target light flux is projected toward an examinee's eye via a fixedly disposed optical element, a change in position of the target light flux incident to the optical element is found due to a state of alignment in some cases. When an incident position of the target light flux changes with respect to the optical element, an image location of the target light flux moves, and thus a projection magnification of the examination target presented to the examinee's eye changes. Therefore, even when the examinee's eye and the subjective optometry apparatus are appropriately aligned, it may not be possible to measure optical characteristics of the examinee's eye.

SUMMARY

An object of this disclosure is to provide a subjective optometry apparatus that enables to perform subjective optometry with ease and accuracy, and a storage medium.

Means for Solving the Problem

In order to solve a problem described above, this disclosure includes the following configuration.

(1) A subjective optometry apparatus that subjectively measures optical characteristics of an examinee's eye, the subjective optometry apparatus including:

a light projecting optical system that projects a target light flux to the examinee's eye;

a fixed optical element that guides an image of the target light flux to the examinee's eye so as to have an optically predetermined examination length;

a calibration optical system disposed in an optical path of the light projecting optical system to change the optical characteristics of the examinee's eye;

a measurement unit that accommodates the light projecting optical system;

a positional information acquiring portion that acquires positional information of the measurement unit;

a correction amount setting portion that sets a correction amount for correcting a projection magnification of the target light flux projected to the examinee's eye, based on the positional information; and a correction portion that corrects the projection magnification of the target light flux, based on the correction amount set by the correction amount setting portion.

(2) The subjective optometry apparatus according to (1) above further including:

a detection portion that detects a length between the examinee's eye and a pupil conjugate position of the light projecting optical system; and an adjustment portion that adjusts a position of the measurement unit in an optical axis direction based on a detection result obtained by the detection portion.

(3) The subjective optometry apparatus according to (1) above, in which the light projecting optical system has a display, and the target light flux is emitted by displaying a target on the display, and the correction portion changes a size of the target displayed on the display, based on the correction amount, to correct the projection magnification of the target light flux.

(4) The subjective optometry apparatus according to (1) above further including:

an optical element that is movable with respect to the optical path of the light projecting optical system; and a drive portion that moves the optical element with respect to the optical path of the light projecting optical system, in which the correction portion controls the drive portion such that the optical element is moved, based on the correction amount, to correct the projection magnification of the target light flux.

(5) The subjective optometry apparatus according to (4) above, in which the correction portion controls the drive portion such that the optical element is moved in an optical axis direction of the light projecting optical system, based on the correction amount, to correct the projection magnification of the target light flux.

(6) The subjective optometry apparatus according to (4) above, in which the correction portion controls the drive portion such that the optical element is inserted into or is removed from the optical path of the light projecting optical system, based on the correction amount, to correct the projection magnification of the target light flux.

(7) The subjective optometry apparatus according to (1) above, in which the fixed optical element is a concave mirror.

(8) The subjective optometry apparatus according to (1) above, in which the fixed optical element guides the target light flux calibrated by the calibration optical system to the examinee's eye.

(9) A storage medium that stores a subjective optometry program used in a subjective optometry apparatus that subjectively measures optical characteristics of an examinee's eye and includes a light projecting optical system that projects a target light flux to the examinee's eye, a fixed optical element that guides an image of the target light flux to the examinee's eye so as to have an optically predetermined examination length, and a calibration optical system disposed in an optical path of the light projecting optical system to change the optical characteristics of the examinee's eye, the subjective optometry program, when executed by a processor of the subjective optometry apparatus, causing the subjective optometry apparatus to execute:

a positional information acquiring step of acquiring positional information of the measurement unit that accommodates the light projecting optical system;

a correction amount setting step of setting a correction amount for correcting a projection magnification of the target light flux projected to the examinee's eye, based on the positional information; and a correcting step of correcting the projection magnification of the target light flux based on the correction amount set in the correction amount setting step.

DETAILED DESCRIPTION

<Overview>

Figure 1:
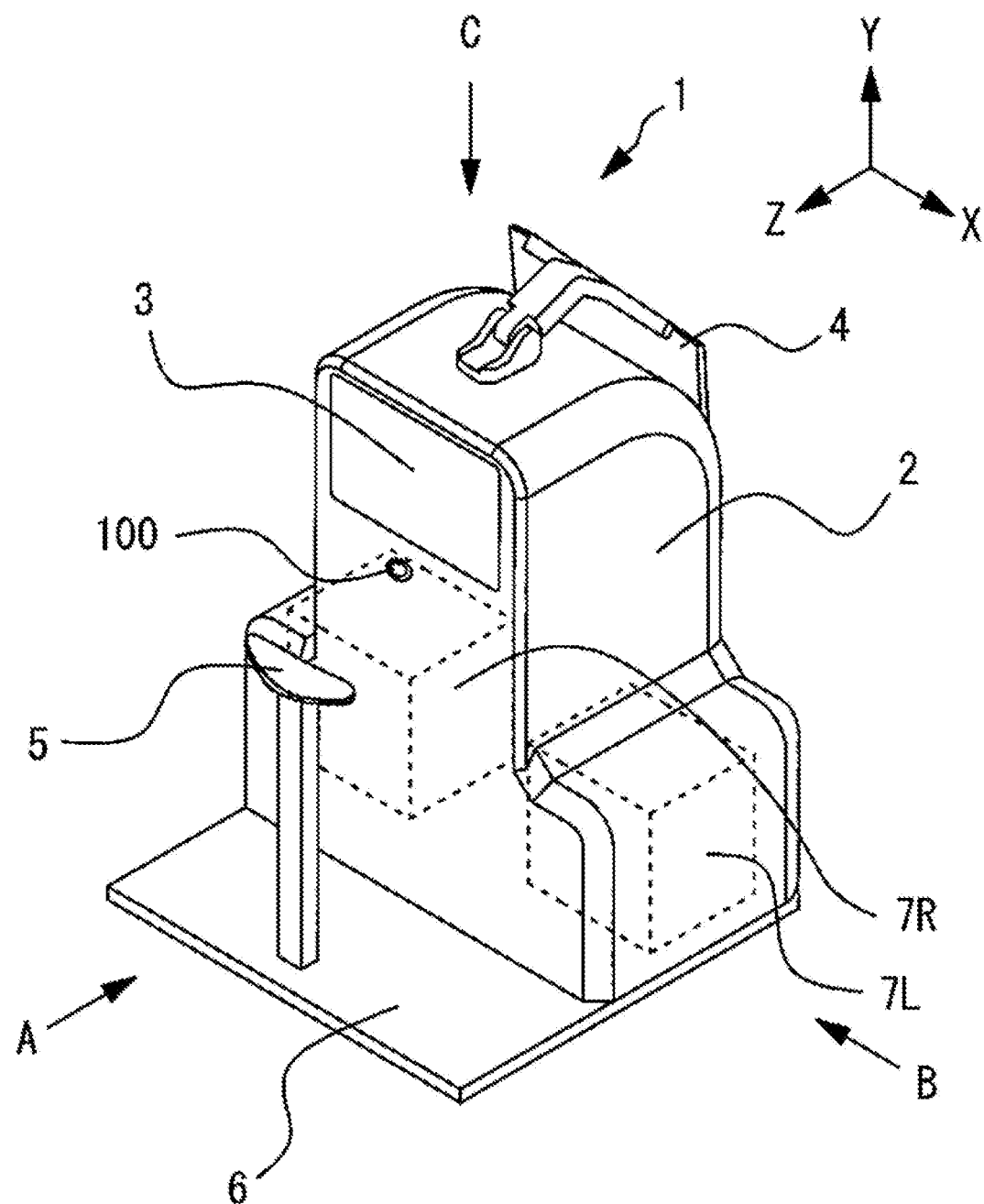
FIG. 1 is a view illustrating the external appearance of a subjective optometry apparatus according to an example.

Hereinafter, one of typical embodiments will be described with reference to the accompanying figures. FIGS. 1 to 12 are views illustrating a subjective optometry apparatus according to this embodiment. This disclosure is not limited to an apparatus described in this example. For example, terminal control software (a program) that performs a function of an example to be described below can be supplied to a system or an apparatus via a network, various types of storage media, or the like, and a control device (for example, a CPU or the like) of the system or the apparatus can also read and execute the program. The following chapters classified by < > are used individually or in association with each other.

In the following description, a depth direction (frontward-rearward direction of an examinee) of a subjective optometry apparatus is referred to as a Z direction, a horizontal direction (rightward-leftward direction of the examinee) on a plane perpendicular to the depth direction is referred to as an X direction, and a vertical direction (upward-downward direction of the examinee) is referred to as a Y direction. L and R attached to Reference signs indicate that an item is used for the left eye and the right eye, respectively.

For example, a subjective optometry apparatus (for example, a subjective optometry apparatus 1) in this embodiment includes a light projecting optical system (for example, a light projecting optical system 30) and a calibration optical system (for example, a calibration optical system 60 or a subjective measurement optical system 25) and subjectively measures optical characteristics of an examinee's eye.

An example of optical characteristics of an examinee's eye, which is subjectively measured, may include at least one of eye refractive power (for example, at least one of a spherical diopter power, an astigmatic power, an astigmatic axis angle, and the like), contrast sensitivity, a vision function of both eyes (for example, at least one of a degree of heterophoria, a stereo-vision function, and the like), and the like.

For example, the light projecting optical system projects the target light flux toward an examinee's eye. For example, the calibration optical system is disposed in an optical path of the light projecting optical system and changes the optical characteristics of the target light flux. The light projecting optical system does not need to be integrally provided in the subjective optometry apparatus, and a configuration, in which a device includes a light projecting optical system that is separately provided, may be employed. That is, the subjective optometry apparatus in this embodiment may be configured to include at least the calibration optical system.

<Light Projecting Optical System>

For example, the light projecting optical system includes a light source that performs irradiation with the target light flux. In addition, the light projecting optical system may include at least one optical element that guides, toward the examinee's eye, the target light flux projected from the light source that projects the target light flux.

For example, a configuration in which a display (for example, a display 31) is used as the light source that projects the target light flux may be employed. For example, a liquid crystal display (LCD), an organic electro luminescence (EL), or the like is used as the display. For example, an examination target or the like such as a Landolt ring optotype is displayed on the display.

For example, a digital micromirror device (DMD) may be used as a light source that projects the target light flux. In general, the DMD has a high reflectance and is bright. Therefore, it is possible to maintain the intensity of the target light flux, compared to a case of using a liquid crystal display using polarized light.

For example, the light source that projects the target light flux may be configured to include a visible light source for presenting a target and a target plate. In this case, for example, the target plate is a rotatable disc plate and is provided with a plurality of targets. For example, the plurality of targets include a target for a vision examination or the like which is used during subjective measurement. For example, as the target for the vision examination, a target (a visual acuity value of 0.1, 0.3, . . . , or 1.5) for each visual acuity value is prepared. For example, the target plate rotates by a motor or the like, and the targets are switched and disposed on an optical path along which the target light flux is guided to the examinee's eye. It is needless to say that a light source having another configuration may be used as the light source that projects the target light flux.

For example, in this embodiment, the light projecting optical system may include a right-eye light projecting optical system and a left-eye light projecting optical system provided as a pair on the right and left sides. For example, the right-eye light projecting optical system and the left-eye light projecting optical system may have a configuration in which the right-eye light projecting optical system is configured to include the same members as those of the left-eye light projecting optical system. In addition, for example, the right-eye light projecting optical system and the left-eye light projecting optical system may have a configuration in which at least some members that configure the right-eye light projecting optical system are different from members that configure the left-eye light projecting optical system. For example, the right-eye light projecting optical system and the left-eye light projecting optical system may have a configuration in which at least some members that configure the right-eye light projecting optical system serve as members that configure the left-eye light projecting optical system. In addition, for example, the right-eye light projecting optical system and the left-eye light projecting optical system may have a configuration in which members that configure the right-eye light projecting optical system are separately provided from members that configure the left-eye light projecting optical system.

<Calibration Optical System>

For example, the calibration optical system may be configured to change the optical property of the target light flux (for example, at least one of a spherical diopter power, a cylindrical power, a cylinder axis, a polarization property, an aberration amount, and the like). For example, a configuration of controlling an optical element may be employed as a configuration of changing the optical property of the target light flux. For example, a configuration of using at least one of a spherical lens, a cylinder lens, a cross cylinder lens, a rotary prism, a wavefront modulation element, or the like may be employed as the optical element. For example, it is needless to say that an optical element that is different from the optical element described above may be used as the optical element.

For example, the calibration optical system may have a configuration in which a spherical diopter power of an examinee's eye is calibrated by optically changing a presentation position (presentation length) of a target with respect to an examinee's eye. In this case, for example, a configuration of moving the light source (for example, the display) in an optical axis direction may be employed as the configuration of optically changing the presentation position (presentation length) of the target. In addition, in this case, a configuration of moving, in the optical axis direction, the optical element (for example, a spherical lens) disposed in the optical path may be employed. It is needless to say that the calibration optical system may have a configuration obtained by combining the configuration of controlling the optical element and the configuration of moving, in the optical axis direction, the optical element disposed in the optical path.

For example, an optometry unit (phoropter) that switches and disposes an optical element that is disposed in front of an examinee's eye may be used as the calibration optical system. For example, the optometry unit may include a lens disc in which a plurality of optical elements are disposed on the same circumference thereof and a drive portion for rotating the lens disc and may be configured to electrically switch the optical elements by the drive of the drive portion (for example, a motor).

For example, the calibration optical system may employ a configuration in which the optical element is disposed between the optical element for guiding the target light flux from the light projecting optical system toward the examinee's eye and the light source of the light projecting optical system such that the optical element is controlled, and thereby the optical characteristics of the target light flux are changed. That is, the calibration portion may have a configuration of a phantom lens refractometer (phantom calibration optical system). In this case, for example, a target light flux calibrated by the calibration optical system is guided to the examinee's eye via the optical element.

For example, in this embodiment, the calibration optical system includes a right-eye calibration optical system and a left-eye calibration optical system provided as a pair on the right and left sides. For example, the right-eye calibration optical system and the left-eye calibration optical system may have a configuration in which the right-eye calibration optical system is configured to include the same members as those of the left-eye calibration optical system. In addition, for example, the right-eye calibration optical system and the left-eye calibration optical system may have a configuration in which at least some members that configure the right-eye calibration optical system are different from members that configure the left-eye calibration optical system. For example, the right-eye calibration optical system and the left-eye calibration optical system may have a configuration in which at least some members that configure the right-eye calibration optical system serve as members that configure the left-eye calibration optical system. In addition, for example, the right-eye calibration optical system and the left-eye calibration optical system may have a configuration in which members that configure the right-eye calibration optical system are separately provided from members that configure the left-eye calibration optical system.

<Projection Magnification Correction of Target Light Flux Based on Positional Deviation and Eye Refractive Power of Examinee's Eye>

For example, the subjective optometry apparatus in this embodiment may include an acquiring portion (for example, a controller 70) that acquires a calibration power of the calibration optical system. For example, the subjective optometry apparatus in this embodiment may include a detection portion (for example, the controller 70) that detects a length between the examinee's eye and a pupil conjugate position of the light projecting optical system. In addition, for example, the subjective optometry apparatus may include a correction amount setting portion (for example, the controller 70) that sets a correction amount for correcting a projection magnification of the target light flux that is projected to the examinee's eye, based on a detection result detected by the detection portion and the calibration power acquired by the acquiring portion. In addition, for example, the subjective optometry apparatus may include a correction portion (for example, the controller 70) that corrects the projection magnification of the target light flux, based on the correction amount set by the correction amount setting portion.

According to the configuration described above, an examiner can reduce a change in size of a target due to a deviation of the examinee's eye from the pupil conjugate position and the eye refractive power of the examinee's eye so as to subjectively measure the optical characteristics of the examinee's eye. Therefore, the examiner can perform subjective measurement with accuracy.

In addition, for example, in a case where a position of the examinee's eye moves or the like, it is difficult to perform the position adjustment of the pupil conjugate position of the light projecting optical system with respect to the examinee's eye. Even in this case, it is possible to present the target in the same size as the size of the target that can be observed when the position adjustment of the examinee's eye to the pupil conjugate position is performed. In this manner, when the position of the examinee's eye deviates, the size of the target is likely to change, and thus it is possible to suppress a state in which the examinee is difficult to observe the target. That is, the examiner can perform subjective measurement with accuracy.

For example, the detection portion may have a configuration of measuring the length between the examinee's eye (for example, the apex of the cornea of the examinee's eye or the pupil position of the examinee's eye) and the pupil conjugate position of the light projecting optical system, as a configuration of measuring the length between the examinee's eye and the pupil conjugate position of the light projecting optical system. In addition, for example, the detection portion may have a configuration of measuring an alignment state of the examinee's eye, as the configuration of measuring the length between the examinee's eye and the pupil conjugate position of the light projecting optical system. In this case, for example, an alignment reference position is set, and a deviation amount from the alignment reference position is measured. In this manner, the alignment state of the examinee's eye may be measured. The alignment reference position is a position at which the alignment state is appropriate (for example, appropriate position adjustment of the examinee's eye and the measurement unit that accommodates the light projecting optical system is performed). In other words, the position adjustment of the examinee's eye is performed at the alignment reference position, and thereby the alignment state becomes appropriate. In this manner the pupil position of the examinee's eye in emmetropia (the examinee's eye having the eye refractive power of 0 D) is coincident with the pupil conjugate position. In addition, for example, a length from the examinee's eye to a predetermined member (for example, a presentation window 3, a measurement unit 7, or the like) in the subjective optometry apparatus 1 when the position adjustment of the examinee's eye is performed at the alignment reference position may be used as an operation length. In this case, for example, the alignment reference position is a position at which the operation length between the examinee's eye and the subjective optometry apparatus 1 is an appropriate operation length. In a case where the operation length between the examinee's eye and the subjective optometry apparatus 1 is the appropriate operation length, a configuration in which the pupil position of the examinee's eye in emmetropia (the examinee's eye having the eye refractive power of 0 D) is coincident with the pupil conjugate position.

For example, the calibration power of the calibration optical system may be set by acquiring the eye refractive power of the examinee's eye in advance and controlling the calibration optical system based on the eye refractive power. In this case, for example, the subjective optometry apparatus may include an eye refractive power acquiring portion that acquires the eye refractive power of the examinee's eye. For example, the calibration optical system may be controlled, based on the eye refractive power acquired by the eye refractive power acquiring portion. After the calibration optical system is controlled, the calibration power may be acquired by the calibration optical system such that a correction amount is set.

For example, the eye refractive power acquiring portion may be configured to acquire an eye refractive power of the examinee's eye by measuring the eye refractive power by an objective measurement optical system (for example, an objective measurement optical system 10) provided in the subjective optometry apparatus. In addition, for example, the eye refractive power acquiring portion may be configured to acquire an eye refractive power of the examinee's eye by measuring the eye refractive power acquired by a subjective measurement optical system (for example, an subjective measurement optical system 25) provided in the subjective optometry apparatus. In this case, for example, the eye refractive power may be an eye refractive power that is acquired at a timing of the subjective measurement. In addition, in this case, for example, the eye refractive power may be an eye refractive power that is measured at a timing different from the subjective measurement. In addition, for example, the eye refractive power acquiring portion may be configured to acquire an eye refractive power of the examinee's eye by receiving the eye refractive power measured by an objective measurement optical system or a subjective measurement optical system of a separate apparatus from the subjective optometry apparatus. In addition, for example, the eye refractive power acquiring portion may be configured to acquire an eye refractive power of the examinee's eye by receiving the eye refractive power input by an examiner when the examiner operates operating means.

For example, the correction amount setting portion may be configured to set a correction amount in advance based on the eye refractive power and the length between the examinee's eye and the pupil conjugate position of the light projecting optical system. In this case, for example, a correction table based on the eye refractive power and the length between the examinee's eye and the pupil conjugate position of the light projecting optical system may be stored in a storage portion (for example, a memory 75), and a call of a correction amount may performed from the storage portion. In this manner, the correction amount may be set. For example, the correction amount setting portion may be configured to perform a calculation process and calculate a correction amount based on the eye refractive power and the length between the examinee's eye and the pupil conjugate position of the light projecting optical system.

<Projection Magnification Correction of Target Light Flux Based on Position Adjustment of Examinee's Eye and Pupil Conjugate Position>

For example, the subjective optometry apparatus may include a fixed optical element (for example, a concave mirror 85) that guides an image of the target light flux to the examinee's eye so as to have an optically predetermined examination length. In addition, for example, the subjective optometry apparatus may include the measurement unit (for example, the measurement unit 7) that accommodates the light projecting optical system. In addition, for example, the subjective optometry apparatus may include a positional information acquiring portion (for example, the controller 70) that acquires positional information of the measurement unit. For example, the subjective optometry apparatus may include the correction amount setting portion (for example, the controller 70) that sets a correction amount for correcting a projection magnification of a target light flux that is projected to the examinee's eye, based on the positional information. In addition, for example, the subjective optometry apparatus may include a correction portion (for example, the controller 70) that corrects the projection magnification of the target light flux, based on the correction amount set by the correction amount setting portion. For example, according to such a configuration described above, in the subjective optometry apparatus including the fixed optical element, when adjusting the deviation between the examinee's eye and the pupil conjugate position of the light projecting optical system, the examiner can project the target having the same size to the examinee's eye even in a case where the projection magnification of the target that is projected to the examinee's eye is changed. Therefore, the examiner can perform subjective measurement on the examinee's eye with accuracy.

In addition, for example, the correction amount setting portion that sets the correction amount for correcting the projection magnification of the target light flux that is projected to the examinee's eye, based on the positional information, may be configured to have at least some members which serve as members in a correction amount setting portion that sets a correction amount for correcting a projection magnification of the target light flux that is projected to the examinee's eye, based on a detection result detected by the detection portion and the calibration power of the calibration optical system which is acquired by the acquiring portion. It is needless to say that a configuration, in which both of the correction amount setting portions described above are separately provided, may be employed.

For example, the fixed optical element may be disposed to be fixed to an apparatus main body. For example, the apparatus main body may be fixedly disposed with respect to the examinee's eye. For example, the fixed optical element may be configured to guide the target light flux calibrated by the calibration optical system to the examinee's eye.

For example, a concave mirror may be used as the fixed optical element. For example, it is possible to present the target at an optically predetermined examination length in subjective examination means by using the concave mirror, and there is no need to dispose a member or the like such that the predetermined examination length becomes an actual length when the target is presented at the predetermined examination length. In this manner, there is no need to provide an extra member and a space, and thus it is possible to reduce the apparatus in size. It is needless to say that the fixed optical element is not limited to the concave mirror. For example, the fixed optical element may be configured to guide an image of the target light flux to the examinee's eye so as to have the predetermined optically examination length. In this case, for example, a lens or the like may be used as the fixed optical element.

For example, the positional information acquiring portion may be configured to acquire the positional information of the measurement unit. For example, a configuration of detecting movement of the measurement unit (for example, positional information of the measurement unit) may be employed as the configuration of acquiring the positional information of the measurement unit. A configuration of detecting the position of the measurement unit or a configuration of detecting a movement amount of the measurement unit may be employed as the configuration of detecting the positional information of the measurement unit. The positional information of the measurement unit may be positional information of the entire measurement unit or may be positional information of at least one member of the light projecting optical system accommodated in the measurement unit. In addition, the positional information of the measurement unit may be positional information of an optical element that is moved along with the measurement unit in the subjective optometry apparatus 1. In this case, the optical element that is moved along with the measurement unit may be configured to integrally move with the measurement unit.

In addition, an example of a configuration of acquiring positional information of the measurement unit may include a configuration of acquiring relative positional information between the examinee's eye (for example, the apex of the cornea of the examinee's eye or the pupil position of the examinee's eye) and the measurement unit. For example, in a case of acquiring the relative positional information between the examinee's eye and the measurement unit, the positional information acquiring portion may be configured to acquire the relative positional information by detecting both of the position of the examinee's eye and the position of the measurement unit. For example, in a case of acquiring the relative positional information between the examinee's eye and the measurement unit, the positional information acquiring portion may be configured to acquire the relative positional information by detecting the position of the measurement unit. In this case, for example, the position of the examinee's eye may be stored in the storage portion in advance. In addition, for example, the positional information acquiring portion may be configured to acquire the relative positional information by detecting the movement amount of the measurement unit. In this case, for example, the movement amount of the measurement unit from a preset initial position may be detected. The positional information of the measurement unit may be positional information of the entire measurement unit or may be positional information of at least one member of the light projecting optical system accommodated in the measurement unit.

In addition, for example, a configuration of acquiring positional information of the measurement unit by acquiring the relative positional information between the fixed optical element and the measurement unit may be employed as the configuration of acquiring the positional information of the measurement unit. For example, in a case of acquiring the relative positional information between the fixed optical element and the measurement unit, the positional information acquiring portion may be configured to acquire the relative positional information by detecting both of the position of the fixed optical element and the position of the measurement unit. For example, in the case of acquiring the relative positional information between the fixed optical element and the measurement unit, the positional information acquiring portion may be configured to acquire the relative positional information by detecting the position of the measurement unit. In this case, for example, the position of the fixed optical element may be stored in the storage portion in advance. In addition, for example, the positional information acquiring portion may be configured to acquire the relative positional information by detecting the movement amount of the measurement unit. In this case, for example, the movement amount of the measurement unit from the preset initial position may be detected. The positional information of the measurement unit may be positional information of the entire measurement unit or may be positional information of at least one element of the light projecting optical system accommodated in the measurement unit.

For example, the correction amount setting portion may be configured to set a correction amount in advance based on the relative positional information. In this case, for example, a correction table based on the relative positional information may be stored in the storage portion, and a call of a correction amount may performed from the storage portion. In this manner, the correction amount may be set. In addition, for example, the correction amount setting portion may be configured to perform the calculation process and to calculate a correction amount based on the relative positional information.

For example, the subjective optometry apparatus may include a detection portion (for example, the controller 70) that detects the length between the examinee's eye and the pupil conjugate position of the light projecting optical system. In addition, for example, the subjective optometry apparatus may include adjustment portions (for example, a left-eye drive portion 9L and a right-eye drive portion 9R) that adjust a position of the measurement unit with respect to the fixed optical element in an optical axis direction, based on a detection result by the detection portion. In this manner, in a case where the position of the examinee's eye deviates, a length between the fixed optical element and the measurement unit is automatically adjusted such that the pupil conjugate position of the light projecting optical system is coincident with the examinee's eye. Therefore, the examiner can easily align the measurement unit with the examinee's eye.

For example, the detection portion that detects the length between the examinee's eye and the pupil conjugate position of the light projecting optical system may have a configuration of measuring the length between the examinee's eye (for example, the apex of the cornea of the examinee's eye or the pupil position of the examinee's eye) and the pupil conjugate position of the light projecting optical system, as a configuration of measuring the length between the examinee's eye and the pupil conjugate position of the light projecting optical system. In addition, for example, the detection portion may have a configuration of measuring the alignment state of the examinee's eye, as the configuration of measuring the length between the examinee's eye and the pupil conjugate position of the light projecting optical system.

The configuration of adjusting the position of the measurement unit based on the detection result by the detection portion is exemplified; however, the configuration is not limited thereto. For example, the adjustment portion may be configured to manually adjust the position of the measurement unit in the optical axis direction. In this case, for example, the adjustment portion may be configured to adjust the position of the measurement unit by operating an operating portion.

For example, the adjustment of the position of the measurement unit may be performed by a configuration in which it is possible to move the pupil conjugate position of the light projecting optical system by moving at least some members of the light projecting optical system accommodated in the measurement unit.

<Correction Portion>

For example, the correction portion may be configured to correct the projection magnification of the target light flux by changing the size of the target that is displayed on the display (for example, the display 31), based on the correction amount. In this case, the light projecting optical system may be configured to have the display, and the target light flux may be emitted by displaying the target on the display. For example, with the configuration of changing the size of the target that is displayed on the display, based on the set correction amount, the examiner can easily correct the projection magnification of the target light flux.

In addition, for example, the correction portion may correct the projection magnification of the target light flux by controlling the drive portion such that the optical element is moved, based on the correction amount. In this case, for example, a configuration of including an optical element that is movable in the optical path of the light projecting optical system and a drive portion that moves the optical element along the optical path of the light projecting optical system may be employed. For example, a lens, a prism, a mirror, or the like may be used as the optical element. In addition, for example, the optical element may be any optical element in the light projecting optical system or may be an optical element provided as a separate member from the light projecting optical system. For example, according to such a configuration, the examiner can dispose the optical element at an appropriate position with respect to the examinee's eye and correct the projection magnification of the target light flux with accuracy.

In addition, for example, the correction portion may have a configuration of correcting the projection magnification of the target light flux by controlling the drive portion such that the optical element is moved in the optical axis direction of the light projecting optical system, based on the correction amount, as the configuration of controlling the drive portion such that the optical element is moved. In this manner, for example, the examiner can correct the projection magnification of the target light flux with a simple configuration. In addition, for example, the correction portion may have a configuration of correcting the projection magnification of the target light flux by controlling the drive portion based on the correction amount such that the optical element is inserted into and is removed from the optical path of the light projecting optical system, as the configuration of controlling the drive portion such that the optical element is moved. In this manner, for example, the examiner can correct the projection magnification of the target light flux with a simple configuration.

Example

Hereinafter, the subjective optometry apparatus in this example will be described. For example, the subjective optometry apparatus may include a subjective measurement portion. In this case, for example, the subjective optometry apparatus may include an objective measurement portion. In this example, the subjective optometry apparatus including both of the subjective measurement portion and the objective measurement portion is exemplified and described.

FIG. 1 is a view illustrating the external appearance of the subjective optometry apparatus 1 according to this example. For example, the subjective optometry apparatus 1 includes a housing 2, a presentation window 3, a monitor 4, a chin rest 5, a base 6, an anterior chamber imaging optical system 100, and the like. For example, the housing 2 includes the measurement unit 7 inside (which will be described below in detail). For example, the presentation window 3 is used to present the target to the examinee. For example, the target light flux from the measurement unit 7 is projected to an examinee's eye E via the presentation window 3.

For example, the optical property result of the examinee's eye E (for example, spherical refractivity S, cylindrical refractivity C, an astigmatic axis angle A, or the like) is displayed on the monitor (display) 4. For example, the monitor 4 is a touch panel. That is, in this example, the monitor 4 functions as an operating portion (controller). For example, a signal in response to an operation instruction input from the monitor 4 is output to the controller 70 which will be described below. A configuration, in which the monitor 4 is not the touch panel and the monitor 4 and the operating portion are separately provided, may be employed. For example, in this case, a configuration in which at least one of operating portions such as a mouse, a joystick, or a keyboard is used as the operating portion may be employed.

For example, the monitor 4 may be a display mounted on the housing 2 or may be a display connected to the housing 2. For example, in this case, a configuration of using a display of a personal computer may be employed. In addition, a plurality of displays may be used in combination.

For example, a length between the examinee's eye E and the subjective optometry apparatus 1 is constantly maintained by the chin rest 5. In this example, a configuration of using the chin rest 5 for maintaining the length between the examinee's eye E and the subjective optometry apparatus 1 constantly is exemplified and described; however, the configuration is not limited thereto. For example, this example may employ a configuration of using a forehead rest, a face rest, or the like for maintaining the length between the examinee's eye E and the subjective optometry apparatus 1 constantly. For example, the chin rest 5 and the housing 2 are fixed to the base 6.

For example, the anterior chamber imaging optical system 100 may be configured to have an imaging element and a lens (not illustrated). For example, the anterior chamber imaging optical system 100 is used to image the face of the examinee.

<Measurement Unit>

For example, the measurement unit 7 includes a measurement portion 7L for left eye and a measurement portion 7R for right eye. For example, the measurement portion 7L for left eye and the measurement portion 7R for right eye in this example include the same members. That is, the subjective optometry apparatus 1 in this example includes a pair of right and left subjective measurement portions and a pair of right and left objective measurement portions. It is needless to say that the measurement portion 7L for left eye and the measurement portion 7R for right eye may be configured to have at least some different members from each other.

Figure 2:
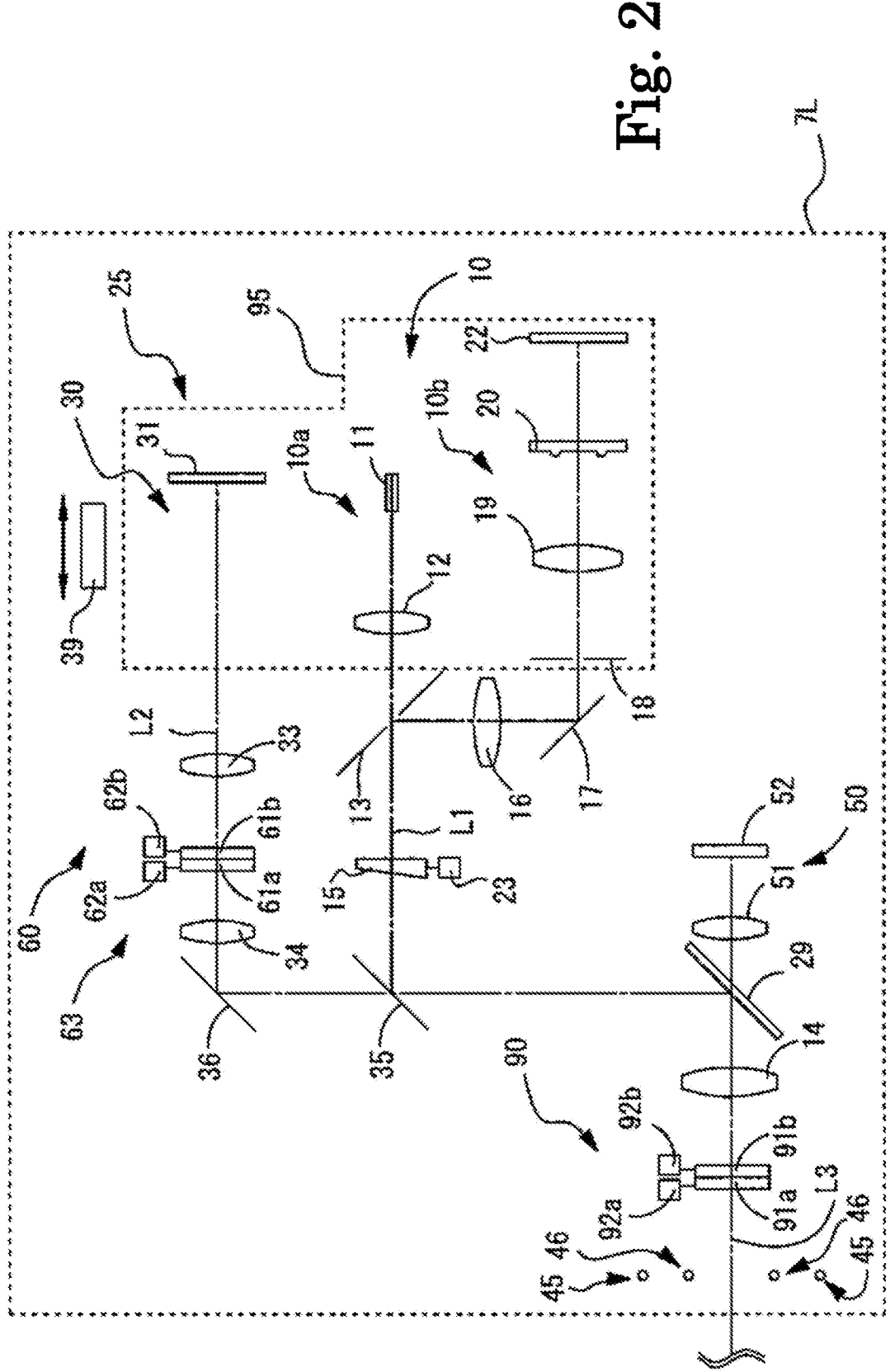
FIG. 2 is a view illustrating a configuration of a measurement unit.

FIG. 2 is a view illustrating a configuration of the measurement unit 7. For example, in this example, the measurement portion 7L for left eye is exemplified and described. The measurement portion 7R for right eye has the same configuration as the measurement portion 7L for left eye, and thus the description thereof is omitted. For example, the measurement portion 7L for left eye includes the subjective measurement optical system 25, the objective measurement optical system 10, a first mark projecting optical system 45, a second mark projecting optical system 46, an observation optical system 50, and the like.

<Subjective Optical System>

For example, the subjective measurement optical system 25 is used as a part of the configuration of the subjective measurement portion that subjectively measures the optical characteristics of the examinee's eye E (which will be described below in detail). Examples of the optical characteristics of the examinee's eye E include the eye refractive power, the contrast sensitivity, the vision function of both eyes (for example, a degree of heterophoria or a stereo-vision function), and the like. In this example, the subjective measurement portion that measures the eye refractive power of examinee's eye E is exemplified and described. For example, the subjective measurement optical system 25 is configured to have a light projecting optical system (target projecting system) 30, the calibration optical system 60, and a correction optical system 90.

For example, the light projecting optical system 30 projects the target light flux toward the examinee's eye E. For example, the light projecting optical system 30 includes the display 31, a projection lens 33, a projection lens 34, a reflective mirror 36, a dichroic mirror 35, a dichroic mirror 29, an objective lens 14, and the like. For example, the target light flux projected from the display 31 is projected to the examinee's eye E through the optical elements of the projection lens 33, the projection lens 34, the reflective mirror 36, the dichroic mirror 35, the dichroic mirror 29, and the objective lens 14 in this order.

For example, an examination target such as a Landolt ring optotype, a fixation target for fixating the examinee's eye E, or the like is displayed on the display 31. For example, the target light flux from the display 31 is projected toward the examinee's eye E. For example, in this example, a case of using a liquid crystal display (LCD) as the display 31 is exemplified and the description thereof is provided below. An organic electro luminescence (EL) display, a plasma display, or the like can be used as the display.

For example, the calibration optical system 60 is disposed in an optical path of the light projecting optical system 30. For example, the calibration optical system 60 changes the optical characteristics of the target light flux. For example, the calibration optical system 60 includes an astigmatism calibrating optical system 63 and a drive mechanism 39. For example, the astigmatism calibrating optical system 63 is disposed between the projection lens 34 and the projection lens 33. For example, the astigmatism calibrating optical system 63 is used to calibrate the cylindrical power, a cylinder axis (astigmatic axis), or the like of the examinee's eye E. For example, the astigmatism calibrating optical system 63 is configured to have two positive cylinder lenses 61a and 61b having the same focal length. The cylinder lens 61a and the cylinder lens 61b are individually rotated around an optical axis L2 by driving performed by rotating mechanisms 62a and 62b, respectively. In this example, a configuration of using the two positive cylinder lenses 61a and 61b as the astigmatism calibrating optical system 63 is exemplified and described; however, the configuration is not limited thereto. The astigmatism calibrating optical system 63 may be configured to calibrate the cylindrical power, the astigmatism axis, or the like. In this case, for example, a configuration in which a calibration lens is disposed in and out of the optical path of the light projecting optical system 30 may be employed.

For example, the drive mechanism 39 is configured to have a motor and a slide mechanism. For example, the drive mechanism 39 moves the display 31 integrally in a direction of the optical axis L2. For example, during the subjective measurement, the display 31 moves, and thereby a presentation position (presentation length) of the target optically changes with respect to the examinee's eye E. In this manner, a spherical refractive power of the examinee's eye E is calibrated. That is, the calibration optical system having the spherical diopter power is configured due to the movement of the display 31. In addition, for example, during the objective measurement, the examinee's eye E is in a fog with the display 31 moving. The calibration optical system having the spherical diopter power is not limited thereto. For example, the calibration optical system having the spherical diopter power may be configured to have a multiple optical elements and to perform calibration by disposing the optical elements in the optical path. In addition, for example, the calibration optical system having the spherical diopter power may be configured to move, in the optical axis direction, the lens disposed in the optical path.

In the example, the calibration optical system that calibrates the spherical diopter power, the cylindrical power, and the cylinder axis is exemplified and described; however, the calibration optical system is not limited thereto. For example, the calibration optical system of which a prism value is calibrated may be provided. The calibration optical system having the prism value is provided, and thereby it is possible to perform calibration such that the target light flux is projected to the examinee's eye even when the examinee's eye is heterophoric.

In this example, a configuration, in which the astigmatism calibrating optical system 63 for calibrating the cylindrical power and the cylinder axis (astigmatic axis) and the calibration optical system (for example, the drive mechanism 39) for calibrating the spherical diopter power are separately provided, is exemplified and described; however, the configuration is not limited thereto. For example, the calibration optical system may be configured to include an optical system that calibrates the spherical diopter power, the cylindrical power, and the astigmatic axis. That is, the calibration optical system in this example may be an optical system that modulates the wavefront. In addition, for example, the calibration optical system may an optical system that calibrates the spherical diopter power, the cylindrical power, the astigmatic axis, or the like. In this case, for example, the calibration optical system is configured to have a lens disc in which multiple optical elements (a spherical lens, a cylinder lens, a dispersing prism, and the like) are disposed on the same circumference. The lens disc is rotated and controlled by a drive portion (actuator or the like), and an optical element (for example, a cylinder lens, a cross cylinder lens, a rotary prism, or the like) that is desired by the examiner is disposed on the optical axis L2 at a rotation angle desired by the examiner. For example, replacement or the like of the optical elements that are disposed on the optical axis L2 may be performed by an operation on the monitor 4 or the like.

The lens disc is formed by one lens disc or a plurality of lens discs. In a case where the plurality of lens discs are disposed, drive portions corresponding to the respective lens discs are provided. For example, each lens disc includes an opening (or a lens of 0 D) and a plurality of optical elements as a lens disc group. Types of the lens discs representatively include a spherical lens disc having a plurality of spherical lenses having different powers, a cylinder lens disc having a plurality of cylinder lenses having different powers, and an auxiliary lens disc having a plurality of types of auxiliary lenses. On the auxiliary lens disc, at least one of a red filter/green filter, a prism, a cross cylinder lens, a polarizer, a Maddox lens, and an auto cross cylinder lens is disposed. In addition, the cylinder lens may be disposed to be rotatable around the optical axis L2 by the drive portion, and the rotary prism and the cross cylinder lens may be disposed to be rotatable around respective optical axes by drive portions.

For example, the correction optical system 90 is disposed between the objective lens 14 and a deflecting mirror 81. For example, the correction optical system 90 is used to correct an optical aberration (for example, astigmatism) occurring in the subjective measurement. For example, the correction optical system 90 is configured to have two positive cylinder lenses 91a and 91b having the same focal length. For example, the correction optical system 90 corrects the astigmatism by adjusting the cylindrical power and the astigmatic axis. The cylinder lens 91a and the cylinder lens 91b are individually rotated around an optical axis L3 by driving performed by rotating mechanisms 92a and 92b, respectively. In this example, a configuration of using the two positive cylinder lenses 91a and 91b as the correction optical system 90 is exemplified and described; however, the configuration is not limited thereto. The correction optical system 90 may be configured to correct the astigmatism. In this case, for example, a configuration in which a correction lens is disposed in and out of the optical axis L3 may be employed.

In this example, a configuration in which the correction optical system 90 is disposed separately from the calibration optical system 60 is exemplified and described; however, the configuration is not limited thereto. For example, a configuration in which the calibration optical system 60 serves as the correction optical system 90 may be employed. In this case, correction for the cylindrical power and the cylinder axis (astigmatic axis) of the examinee's eye E is performed according to an astigmatism amount. That is, the calibration optical system 60 is driven to perform calibration to obtain the cylinder power or the astigmatic axis obtained (corrected) according to the astigmatism amount. For example, the calibration optical system 60 serves as the correction optical system 90, and thereby there is no need to perform complicated control. Therefore, it is possible to correct the optical aberration with a simple configuration. In addition, for example, the calibration optical system 60 serves as the correction optical system 90, and thereby there is no need to provide the correction optical system for the optical aberration. Therefore, it is possible to correct the optical aberration with a simple configuration.

<Objective Optical System>

For example, the objective measurement optical system 10 is used as a part of the configuration of the objective measurement portion that objectively measures the optical characteristics of the examinee's eye (which will be described below in detail). Examples of the optical characteristics of the examinee's eye include an eye refractive power, a length of the eyeball, a shape of the cornea, and the like. In this example, the objective measurement portion that measures the eye refractive power of examinee's eye is exemplified and described. For example, the objective measurement optical system 10 is configured to have a projection optical system 10a, the light receiving optical system 10b, and the correction optical system 90.

For example, the projection optical system (light projecting optical system) 10a projects a measurement mark having a spot shape to the fundus of the examinee's eye E via the central portion of the pupil of the examinee's eye E. For example, the light receiving optical system 10b picks up fundus reflected light reflected from the fundus into a ring shape via a pupil peripheral portion and causes a two-dimensional imaging element 22 to image a ring-shaped fundus reflected image.

For example, the projection optical system 10a includes a measurement light source 11 disposed on an optical axis L1 of the objective measurement optical system 10, a relay lens 12, a hole mirror 13, a prism 15, a drive portion (motor) 23, the dichroic mirror 35, the dichroic mirror 29, and the objective lens 14. For example, the prism 15 is a light flux deflecting member. For example, the drive portion 23 rotatably drives the prism 15 around the optical axis L1. For example, the light source 11 has a conjugate relationship with the fundus of the examinee's eye E. In addition, the hole portion of the hole mirror 13 has a conjugate relationship with the examinee's eye E. For example, the prism 15 is disposed at a position off a conjugate position with the pupil of the examinee's eye E and causes a passing light flux to be eccentric with respect to the optical axis L1. Instead of the prism 15, a parallel flat plate as the light flux deflecting member may be configured to be obliquely disposed on the optical axis L1.

For example, the dichroic mirror 35 is common to the optical path of the subjective measurement optical system 25 and the optical path of the objective measurement optical system 10. That is, for example, the dichroic mirror 35 is coaxial to the optical path L2 of the subjective measurement optical system 25 and the optical path L1 of the objective measurement optical system 10. For example, the dichroic mirror 29 which is an optical path dispersing member reflects the light flux formed by the subjective measurement optical system 25 and measurement light formed by the projection optical system 10*a* and guides the light flux and the measurement light to the examinee's eye E.

For example, the light receiving optical system 10*b* shares the objective lens 14, the dichroic mirror 29, the dichroic mirror 35, the prism 15, and the hole mirror 13 with the projection optical system 10*a* and includes a relay lens 16 disposed in an optical path of the hole mirror 13 in a reflective direction, a mirror 17, a light receiving aperture 18 disposed in an optical path of the mirror 17 in the reflective direction, a collimator lens 19, a ring lens 20, and the two-dimensional imaging element 22 such as a CCD. For example, the light receiving aperture 18 and the two-dimensional imaging element 22 have the conjugate relationship with the fundus of the examinee's eye E. For example, the ring lens 20 is configured to have a lens portion formed to have a ring shape and a light shielding portion on which coating for light shielding is performed in a region other than the lens portion and has an optically conjugate positional relationship with the pupil of the examinee's eye E. For example, an output from the two-dimensional imaging element 22 is input to the controller 70.

For example, the dichroic mirror 29 reflects, toward the light receiving optical system 10*b*, the reflected light of the measurement light from the projection optical system 10*a* which has been guided to the fundus of the examinee's eye E. In addition, for example, the dichroic mirror 29 transmits anterior chamber observing light and alignment light and guides both of the light to the observation optical system 50. For example, the dichroic mirror 35 reflects, toward the light receiving optical system 10*b*, the reflected light of the measurement light from the projection optical system 10*a* which has been guided to the fundus of the examinee's eye E.

The objective measurement optical system 10 is not limited thereto, and a known objective measurement optical system having a configuration of projecting a ring-shaped measurement mark to the fundus from the pupil peripheral portion so as to pick up fundus reflected light from the central portion of the pupil and causing the two-dimensional imaging element 22 to receive light of a ring-shaped fundus reflected image can be used.

The objective measurement optical system 10 is not limited thereto, and a measurement optical system including the light projecting optical system that projects the measurement light toward the fundus of the examinee's eye E and the right receiving optical system that causes a light receiving element to receive the reflected light acquired by reflection of the measurement light from the fundus may be used. For example, an eye refractive power measuring optical system may be configured to have a Shack-Hartmann sensor. It is needless to say that an apparatus including another measurement method (for example, a phase difference type apparatus that projects a slit) may be used.

For example, the light source 11 of the projection optical system 10*a*, the light receiving aperture 18 of the light receiving optical system 10*b*, the collimator lens 19, the ring lens 20, and the two-dimensional imaging element 22 are integrally movable in the optical axis direction. For example, in this example, the light source 11 of the projection optical system 10*a*, the light receiving aperture 18 of the light receiving optical system 10*b*, the collimator lens 19, the ring lens 20, and the two-dimensional imaging element 22 are integrally movable in a direction of the optical axis L1 by the drive mechanism 39 that drives the display 31. That is, the display 31, the light source 11 of the projection optical system 10*a*, the light receiving aperture 18 of the light receiving optical system 10*b*, the collimator lens 19, the ring lens 20, and the two-dimensional imaging element 22 synchronize with a drive unit 95 and integrally move along with the drive unit. It is needless to say that the members described above may be configured to be individually driven.

For example, the drive unit 95 moves a part of the objective measurement optical system 10 in the optical axis direction such that ring light fluxes on the outer side are incident on the two-dimensional imaging element 22 in relation to respective meridian directions. That is, a part of the objective measurement optical system 10 is moved in the direction of the optical axis L1 according to a spherical refraction error (spherical power) of the examinee's eye E, and thereby correction for the spherical refraction error is performed such that the light source 11, the light receiving aperture 18, and the two-dimensional imaging element 22 have an optically conjugate relationship with the fundus of the examinee's eye E. For example, a moving position of the drive mechanism 39 is measured by a potentiometer not illustrated. The hole mirror 13 and the ring lens 20 are disposed to have a conjugate relationship with the pupil of the examinee's eye E at a constant magnification, regardless of the movement amount of the drive unit 95.

According to the configuration described above, the measurement light flux emitted from the light source 11 forms a spot-like point light source image on the fundus of the examinee's eye E through the relay lens 12, the hole mirror 13, the prism 15, the dichroic mirror 35, the dichroic mirror 29, and the objective lens 14. At this time, the prism 15 rotating around the optical axis eccentrically rotates a pupil projection image of the hole portion of the hole mirror 13 (projection light flux on the pupil) at a high speed. The point light source image projected on the fundus is reflected/dispersed to be emitted from the examinee's eye E, is focused by the objective lens 14, and is again focused at the position of the light receiving aperture 18 via the dichroic mirror 29, the dichroic mirror 35, the prism 15 rotating at the high speed, the hole mirror 13, the relay lens 16, and the mirror 17, and a ring-shaped image is formed in the two-dimensional imaging element 22 by the collimator lens 19 and the ring lens 20.

For example, the prism 15 is disposed in a common optical path of the projection optical system 10*a* and the light receiving optical system 10*b*. For example, similar to a configuration of the projection optical system 10*a*, the reflected light flux from the fundus is transmitted through the prism 15, and thus reverse scanning is performed in the following optical systems as though there is no eccentricity of the projection light flux/reflected light flux (receiving light flux).

For example, the correction optical system 90 serves as the subjective measurement optical system 25. It is needless to say that a configuration in which a correction optical system used in the objective measurement optical system 10 is separately provided.

<First Mark Projecting Optical System and Second Mark Projecting Optical System>

For example, in this example, the first mark projecting optical system 45 and the second mark projecting optical system 46 are disposed between the correction optical system 90 and the deflecting mirror 81. It is needless to say that the position of the first mark projecting optical system 45 and the second mark projecting optical system 46 is not limited thereto. For example, the first mark projecting optical system 45 and the second mark projecting optical system 46 may be provided on a cover of the housing 2. For example, in this case, the first mark projecting optical system 45 and the second mark projecting optical system 46 are configured to be disposed around the presentation window 3.

For example, the first mark projecting optical system 45 is provided with a plurality of infrared light sources at a 45-degree interval on a concentric circle around the optical axis L3 and is disposed to be vertically symmetrical with a vertical plane passing through the optical axis L3 interposed therein. For example, the first mark projecting optical system 45 emits near-infrared light for projecting an alignment mark onto the cornea of the examinee's eye E. For example, the second mark projecting optical system 46 is provided with six infrared light sources positioned at a position different from the position of the first mark projecting optical system 45. In this case, the first mark projecting optical system 45 is configured to project a mark of infinity to the cornea of the examinee's eye E, and the second mark projecting optical system 46 is configured to project the mark of a finite distance to the cornea of the examinee's eye E in the upward-downward direction or in an oblique direction. For convenience, only a part of the first mark projecting optical system 45 and the second mark projecting optical system 46 is illustrated in FIG. 2. The second mark projecting optical system 46 may also be used as anterior chamber illumination that illuminates the anterior chamber of the examinee's eye E. In addition, the second mark projecting optical system 46 can be used as the mark for measuring the shape of the cornea. The first mark projecting optical system 45 and the second mark projecting optical system 46 are not limited to the point-like light source. For example, the first mark projecting optical system and the second mark projecting optical system may be a ring-shaped light source or a line-shaped light source.

<Observation Optical System>

For example, the observation optical system (imaging optical system) 50 shares the objective lens 14 and the dichroic mirror 29 with the subjective measurement optical system 25 and the objective measurement optical system 10 and includes an imaging lens 51 and a two-dimensional imaging element 52. For example, the imaging element 52 has an imaging surface disposed at a substantially conjugate position with the anterior chamber of the examinee's eye E. For example, an output from the imaging element 52 is input to the controller 70. In this manner, an anterior chamber image of the examinee's eye E is imaged by the two-dimensional imaging element 52 and is displayed on the monitor 4. The observation optical system 50 serves as an optical system that detects an alignment mark image that is formed on the cornea of the examinee's eye E by the first mark projecting optical system 45 and the second mark projecting optical system 46, and a position of the alignment mark image is detected by the controller 70.

<Internal Configuration of Subjective Optometry Apparatus>

Figure 3:
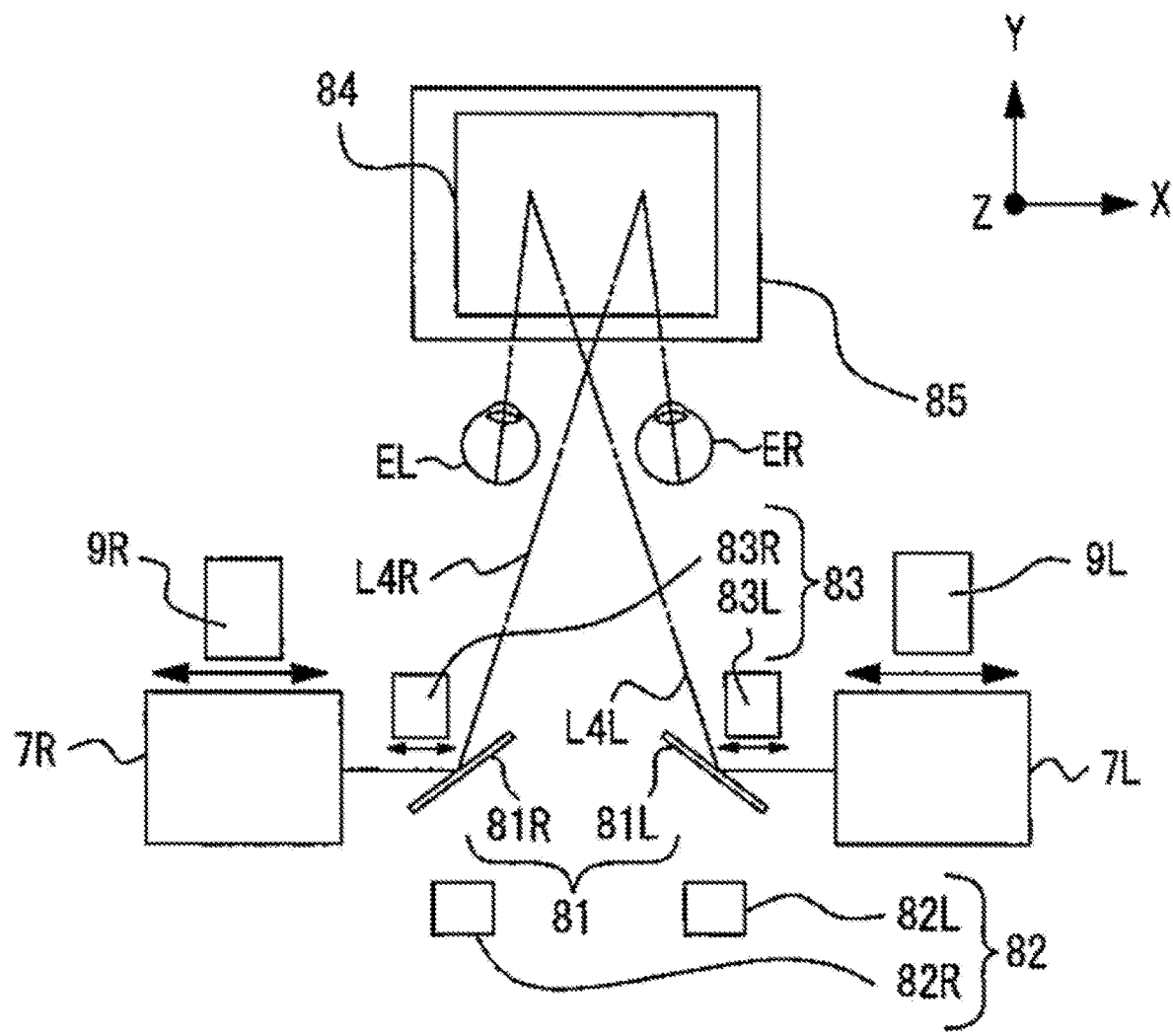
FIG. 3 is a view illustrating a schematic configuration of the inside of the subjective optometry apparatus when viewed from a front direction.
Figure 4:
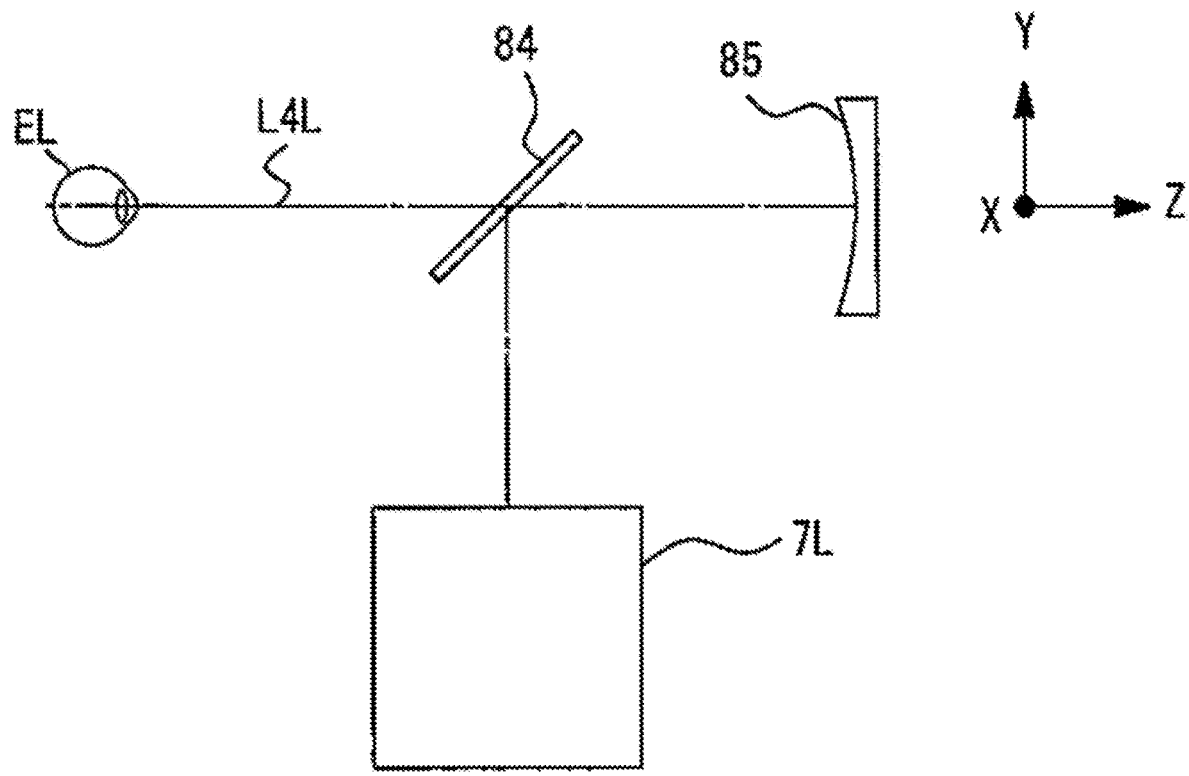
FIG. 4 is a view illustrating a schematic configuration of the inside of the subjective optometry apparatus when viewed from a side direction.
Figure 5:
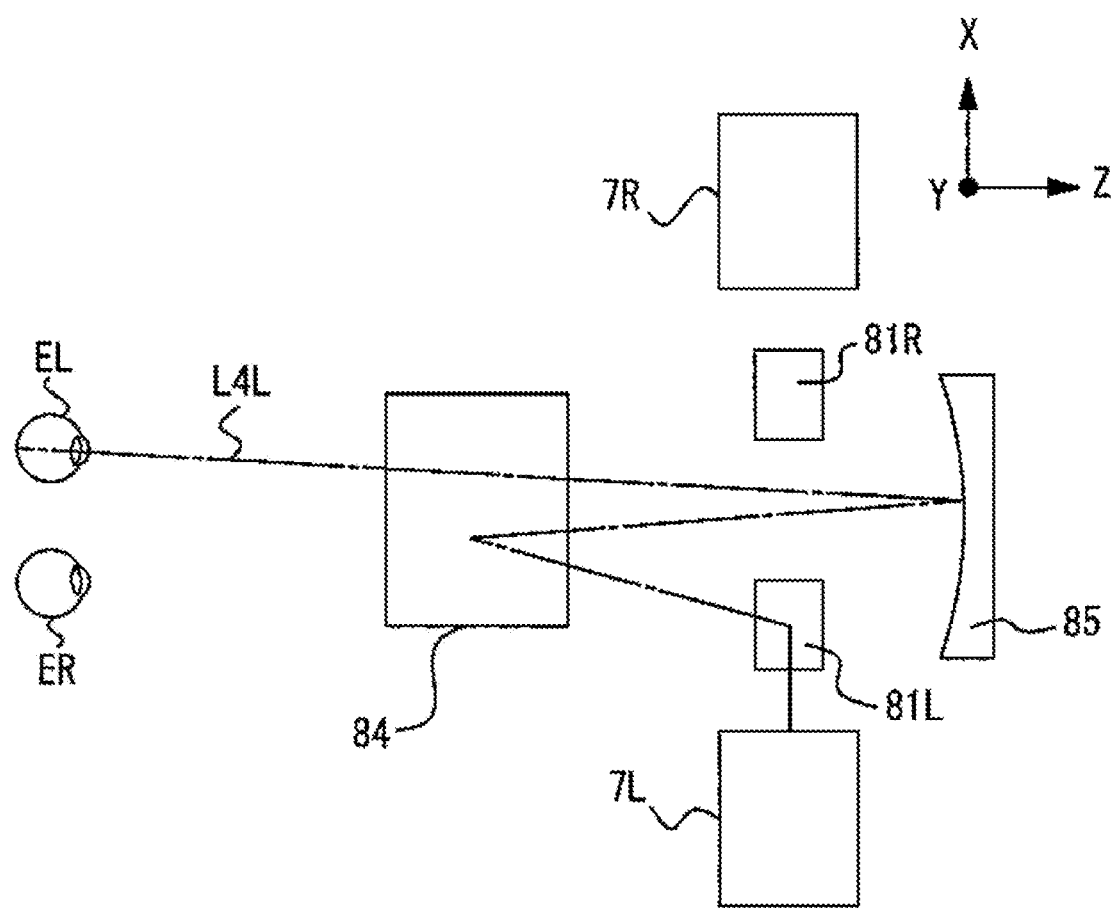
FIG. 5 is a view illustrating a schematic configuration of the inside of the subjective optometry apparatus when viewed from an upper direction.

Hereinafter, an internal configuration of the subjective optometry apparatus 1 will be described. FIG. 3 is a view illustrating a schematic configuration of the inside of the subjective optometry apparatus 1 according to this example when viewed from a front direction (A direction in FIG. 1). FIG. 4 is a view illustrating a schematic configuration of the inside of the subjective optometry apparatus 1 according to this example when viewed from a side direction (B direction in FIG. 1). FIG. 5 is a view illustrating a schematic configuration of the inside of the subjective optometry apparatus 1 according to this example when viewed from an upper direction (C direction in FIG. 1). In FIG. 3, for convenience of description, an optical axis representing reflection from a half mirror 84 is omitted. In FIG. 4, for convenience of description, only an optical axis of the measurement portion 7L for left eye is illustrated. In FIG. 5, for convenience of description, only an optical axis of the measurement portion 7L for left eye is illustrated.

For example, the subjective optometry apparatus 1 includes the subjective measurement portion and the objective measurement portion. For example, the subjective measurement portion is configured to include the measurement unit 7, the deflecting mirror 81, a drive portion 82, a drive portion 83, the half mirror 84, and the concave mirror 85. It is needless to say that the subjective measurement portion is not limited to the configuration. As an example, a configuration, in which the half mirror 84 is not provided, may be employed. In this case, the optical axis of the concave mirror 85 may be irradiated with the light flux in an oblique direction such that a light flux reflected therefrom is guided to the examinee's eye E. For example, the objective measurement portion is configured to include the measurement unit 7, the deflecting mirror 81, the half mirror 84, and the concave mirror 85. It is needless to say that the objective measurement portion is not limited to the configuration. As an example, a configuration, in which the half mirror 84 is not provided, may be employed. In this case, the optical axis of the concave mirror 85 may be irradiated with the light flux in the oblique direction such that a light flux reflected therefrom is guided to the examinee's eye E.

For example, the subjective optometry apparatus 1 includes the left-eye drive portion 9L and the right-eye drive portion 9R and can move both of the measurement portion 7L for left eye and the measurement portion 7R for right eye in the X direction. For example, the measurement portion 7L for left eye and the measurement portion 7R for right eye are moved, thereby, a length between the deflecting mirror 81 and the measurement unit 7 is changed, and the presentation position of the target light flux is changed in the Z direction. In this manner, it is possible to adjust the measurement unit 7 in the Z direction such that the target light flux calibrated by the calibration optical system 60 is guided to the examinee's eye E and the image of the target light flux calibrated by the calibration optical system 60 is formed on the fundus of the examinee's eye E.

For example, the deflecting mirrors 81 are provided as a pair on the right and left side and include a deflecting mirror 81R for the right eye and a deflecting mirror 81L for the left eye. For example, the deflecting mirror 81 is disposed between the calibration optical system 60 and the examinee's eye E. That is, the calibration optical system 60 includes the right-eye calibrating optical system and the left-eye calibration optical system which are provided as a pair on the right and left side, the deflecting mirror 81L for left eye is disposed between the left-eye calibration optical system and the left eye ER, and the deflecting mirror 81R for right eye is disposed between the right-eye calibrating optical system and the right eye ER. For example, it is preferable that the deflecting mirror 81 is disposed at a conjugate position with the pupil.

For example, the deflecting mirror 81L for left eye reflects the light flux that is projected from the measurement portion 7L for left eye and guides the reflected light to the examinee's left eye EL. In addition, for example, the deflecting mirror 81L for left eye reflects the reflected light reflected from the examinee's left eye EL and guides the reflected light to the measurement portion 7L for left eye. For example, the deflecting mirror 81R for right eye reflects the light flux that is projected from the measurement portion 7R for left eye and guides the reflected light to the examinee's right eye ER. In addition, for example, the deflecting mirror 81R for right eye reflects the reflected light reflected from the examinee's right eye ER and guides the reflected light to the measurement portion 7R for right eye. In this example, a configuration of using the deflecting mirror 81 as a deflecting member that reflects the light flux, which is projected from the measurement unit 7, and guides the reflected light to the examinee's eye E is exemplified and described; however, the configuration is not limited thereto. The deflecting member may be a deflecting member that reflects the light flux that is projected from the measurement unit 7 and guides the reflected light to the examinee's eye E. For example, a prism, a lens, or the like is exemplified as the deflecting member.

For example, the drive portion 82 is configured of a motor (drive portion) or the like. For example, the drive portion 82 includes a drive portion 82L for driving the deflecting mirror 81L for left eye and a drive portion 82R for driving the deflecting mirror 81R for right eye. For example, the drive of the drive portion 82 causes the deflecting mirror 81 to rotatably move. For example, the drive portion 82 rotates the deflecting mirror 81 with respect to a rotary shaft in the horizontal direction (X direction) and with respect to a rotary shaft in the vertical direction (Y direction). That is, the drive portion 82 rotates the deflecting mirror 81 in XY directions. The rotation of the deflecting mirror 81 may be performed in one of the horizontal direction or the vertical direction.

For example, the drive portion 83 is configured of a motor (drive portion) or the like. For example, the drive portion 83 includes a drive portion 83L for driving the deflecting mirror 81L for left eye and a drive portion 83R for driving the deflecting mirror 81R for right eye. For example, the drive of the drive portion 83 causes the deflecting mirror 81 to move in the X direction. For example, the deflecting mirror 81L for left eye and the deflecting mirror 81R for right eye are moved, thereby, a length between the deflecting mirror 81L for left eye and the deflecting mirror 81R for right eye is changed, and it is possible to change a length between the left-eye optical path and the right-eye optical path in the X direction, in association with an inter-pupil length of the examinee's eye E.

For example, a plurality of deflecting mirrors may be provided in both of the left-eye optical path and the right-eye optical path. For example, a configuration in which two deflecting mirrors are provided in both of the left-eye optical path and the right-eye optical path (for example, two deflecting mirror or the like in the left eye optical path. In this case, one deflecting mirror may be rotated in the X direction, and another deflecting mirror may be rotated in the Y direction. For example, the deflecting mirror 81 is rotatably moved, and thereby the light flux having a shape for forming the image of the calibration optical system 60 in front of the eye of the examinee is formed in front of the examinee's eye, and thereby it is possible to optically correct the forming position of the image.

For example, the concave mirror 85 is shared between the measurement portion 7R for right eye and the measurement portion 7L for left eye. For example, the concave mirror 85 is shared between the right-eye optical path including the right-eye calibration optical system and the left-eye optical path including the left-eye calibration optical system. That is, the concave mirror 85 is disposed at a position at which the concave mirror passes through both of the right-eye optical path including the right-eye calibration optical system and the left-eye optical path including the left-eye calibration optical system. It is needless to say that the concave mirror 85 may not be configured to be shared between the right-eye optical path and the left-eye optical path. That is, the configuration in which the concave mirror is disposed in both of the right-eye optical path including the right-eye calibration optical system and the left-eye optical path including the left-eye calibration optical system may be employed. For example, the concave mirror 85 guides the target light flux that has passed through the calibration optical system to the examinee's eye E, and the image of the target light flux that has passed through the calibration optical system is formed in front of the examinee's eye E. In this example, the configuration of using the concave mirror 85 may be exemplified and described; however, the configuration is not limited thereto, and it is possible to use types of optical elements. For example, a lens, a flat mirror, or the like may be used as the optical element.

For example, the concave mirror 85 is shared between the subjective measurement portion and the objective measurement portion. For example, the target light flux projected from the subjective measurement optical system 25 is projected to the examinee's eye E via the concave mirror 85. For example, the measurement light projected from the objective measurement optical system 10 is projected to the examinee's eye E via the concave mirror 85. In addition, for example, the reflected light of the measurement light projected from the objective measurement optical system 10 is guided to the light receiving optical system 10b of the objective measurement optical system 10 via the concave mirror 85. In this example, a configuration of guiding the reflected light of the measurement light from the objective measurement optical system 10 to the light receiving optical system 10b of the objective measurement optical system 10 via the concave mirror 85 is exemplified; however, the configuration may not be limited thereto. For example, the reflected light of the measurement light projected from the objective measurement optical system 10 may be projected without the concave mirror 85.

More specifically, for example, in this example, at least an optical axis from the concave mirror 85 in the subjective measurement portion to the examinee's eye E and an optical axis from the concave mirror 85 in the objective measurement portion to the examinee's eye E are configured to be coaxial to each other. For example, in this example, the optical path L2 of the subjective measurement optical system 25 and the optical path L1 of the objective measurement optical system 10 converge to be coaxial to each other by the dichroic mirror 35.

<Optical Path of Subjective Measurement Portion>

Hereinafter, the optical path of the subjective measurement portion will be described. For example, the concave mirror 85 reflects, in a direction to the examinee's eye E, the target light flux having passed through the calibration optical system 60, thereby the subjective measurement portion guides the target light flux to the examinee's eye E, and the image of the target light flux having passed through the calibration optical system 60 is formed in front of the examinee's eye E so as to have an optically predetermined examination length. That is, the concave mirror 85 reflects the target light flux such that the target light flus becomes a substantially parallel light flux. Therefore, the target image viewed from the examinee is viewed to be at a length farther away than an actual length from the examinee's eye E to the display 31. That is, it is possible to present the target image to the examinee such that the image of the target light flux is viewed at a position apart by the predetermined examination length by using the concave mirror 85.

More specific description is provided. The left-eye optical path is exemplified and described in the following description, and the right-eye optical path also has the same configuration as the left-eye optical path. For example, in the subjective measurement portion for left eye, the target light flux projected from the display 13 of the measurement portion 7L for left eye is incident to the astigmatism calibrating optical system 63 via the projection lens 33. The target light flux having passed through the astigmatism calibrating optical system 63 is incident to the correction optical system 90 through the reflective mirror 36, the dichroic mirror 35, the dichroic mirror 29, and the objective lens 14. The target light flux having passed through the correction optical system 90 is projected toward the deflecting mirror 81L for left eye from the measurement portion 7L for left eye. The target light flux that has been emitted from the measurement portion 7L for left eye and has been reflected from the deflecting mirror 81 for left eye is reflected from the half mirror 84 toward the concave mirror 85. The target light flux having reflected from the concave mirror is transmitted through the half mirror 84 and reaches the examinee's left eye EL.

In this manner, the target image calibrated by the calibration optical system 60 is formed on the fundus of the examinee's left eye EL with a glasses wearing position of the examinee's left eye EL (for example, about 12 mm from the apex of the cornea) as a reference. Hence, disposing the astigmatism calibrating optical system 63 as though the astigmatism calibrating optical system is in front of the eye is equivalent to adjusting the spherical diopter power in front of the eye by a calibration optical system of the spherical diopter power (drive of the drive mechanism 39 in this example), and thereby the examinee can collimate the image of the target at a natural state via the concave mirror 85. In this example, the right-eye optical path also has the same configuration as the left-eye optical path, and thereby the target image calibrated by the pair of right and left calibration optical system 60 is formed on the fundi of both of the examinee's eyes with the glasses wearing position of the examinee's right and left eyes ER and EL (for example, about 12 mm from the apex of the cornea) as a reference. In this state, the examinee makes a response to the examiner while directly viewing the target at a natural view state, calibration by the calibration optical system 60 is achieved until the examination target is appropriately viewed, and the optical characteristics of the examinee's eye are subjectively measured, based on a calibration value thereof.

<Optical Path of Objective Measurement Portion>

Subsequently, the optical path of the objective measurement portion will be described. The left-eye optical path is exemplified and described in the following description, and the right-eye optical path also has the same configuration as the left-eye optical path. For example, in the objective measurement portion for left eye, the measurement light emitted from the light source 11 of the projection optical system 10a in the objective measurement optical system 10 is incident to the correction optical system 90 from the relay lens 12 to the objective lens 14. The measurement light having passed through the correction optical system 90 is projected toward the deflecting mirror 81L for left eye from the measurement portion 7L for left eye. The measurement light that has been emitted from the measurement portion 7L for left eye and has been reflected from the deflecting mirror 81 for left eye is reflected from the half mirror 84 toward the concave mirror 85. The measurement light having reflected from the concave mirror is transmitted through the half mirror 84 and reaches the examinee's left eye EL, and a spot-shaped point light source image is formed on the fundus of the examinee's left eye EL. At this time, the prism 15 rotating around the optical axis eccentrically rotates a pupil projection image of the hole portion of the hole mirror 13 (projection light flux on the pupil) at a high speed.

The light of the point light source image formed on the fundus of the examinee's left eye EL is reflected/dispersed to be emitted from the examinee's eye E, is focused by the objective lens 14 through the optical path through which the measurement light has passed, and passes through the dichroic mirror 29, the dichroic mirror 35, the prism 15, the hole mirror 13, the relay lens 16, and the mirror 17. The reflected light having passed through the mirror 17 is again focused on the opening of the light receiving aperture 18, is formed as a substantially parallel light flux (in a case of emmetropia) through the collimator lens 19, is picked up as the ring-shaped light flux by the ring lens 20, and is received as a ring image by the imaging element 22. It is possible to objectively measure the optical characteristics of the examinee's eye E by analyzing the received ring image.

<Controller>

Figure 6:
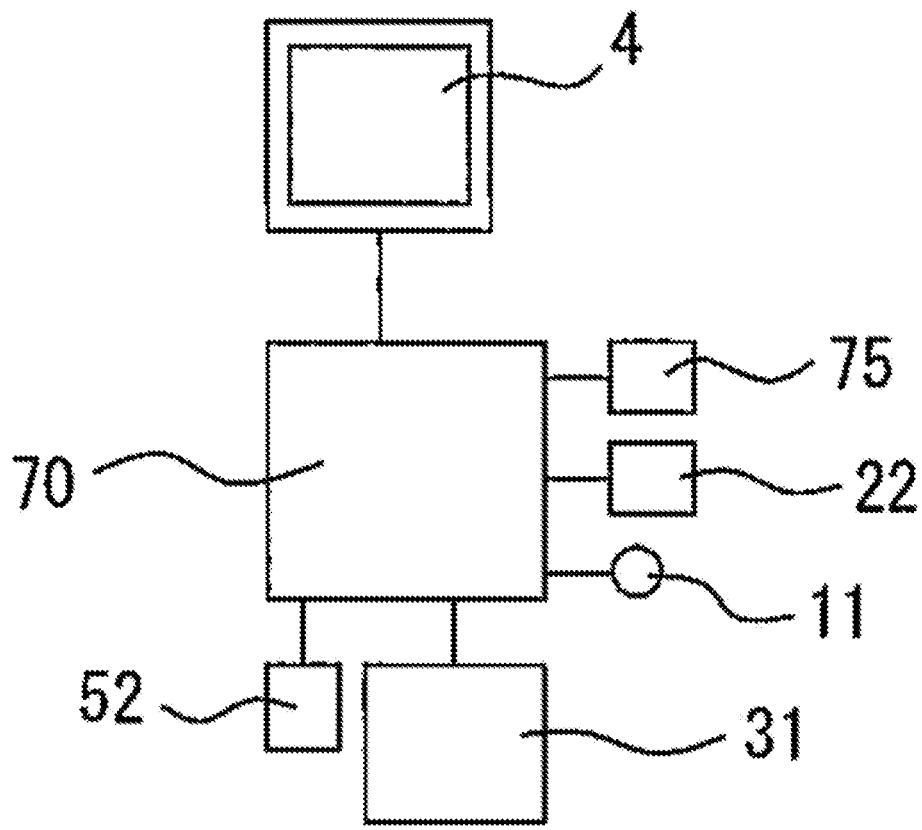
FIG. 6 is a view illustrating a control system of the subjective optometry apparatus.

FIG. 6 is a view illustrating a control system of the subjective optometry apparatus 1 according to this example. For example, various types of members such as the monitor 4, a non-volatile memory 75 (hereinafter, a memory 75), the measurement light source 11 provided in the measurement unit 7, the imaging element 22, the display 31, and the two-dimensional imaging element 52 are electrically connected to the controller 70. In addition, for example, respective drive portions (not illustrated) provided in the drive portion 9, the drive mechanism 39, the rotating mechanisms 62a and 62b, the drive portion 83, and the rotating mechanisms 92a and 92b are electrically connected to the controller 70.

For example, the controller 70 includes a CPU (processor), a RAM, a ROM, and the like. For example, the CPU controls the members in the subjective optometry apparatus 1. For example, the RAM temporarily stores information. For example, in the ROM, various programs for controlling operations of the subjective optometry apparatus 1, target data for various types of examinations, initial values, or the like is stored. The controller 70 may be configured to have a plurality of controllers (that is, a plurality of processors).

For example, the memory 75 is a non-transitory storage medium that is capable of storing the storage content even when electric power supply is cut off. For example, a hard disk drive, a flash ROM, a USB memory that is removably installed in the subjective optometry apparatus 1, or the like can be used as the memory 75. For example, the memory 75 stores control programs for controlling the subjective measurement portion and the objective measurement portion.

<Control Operation>

Operations of the subjective optometry apparatus 1 having the configuration described above are described. For example, in this example, before performing the subjective measurement, the objective measurement on the examinee's eye E is performed by using the objective measurement optical system having the configuration described above. In this case, for example, the controller 70 acquires a subjectively measured refractive power such as a spherical reflectivity S, a cylindrical reflectivity C, an astigmatic axis angle A, or a prism amount Δ of the examinee's eye E. That is, the controller 70 acquires an objective eye refractive power (objective value) of the examinee's eye E. In addition, for example, the controller 70 stores the objective value in the memory 75. For example, in the subjective measurement which will be described below, the calibration optical system 60 is controlled, based on the acquired eye refractive power, and the measurement is started with the state in which the examinee's eye E is calibrated, as the initial state, when the subjective measurement is performed.

Figure 7:
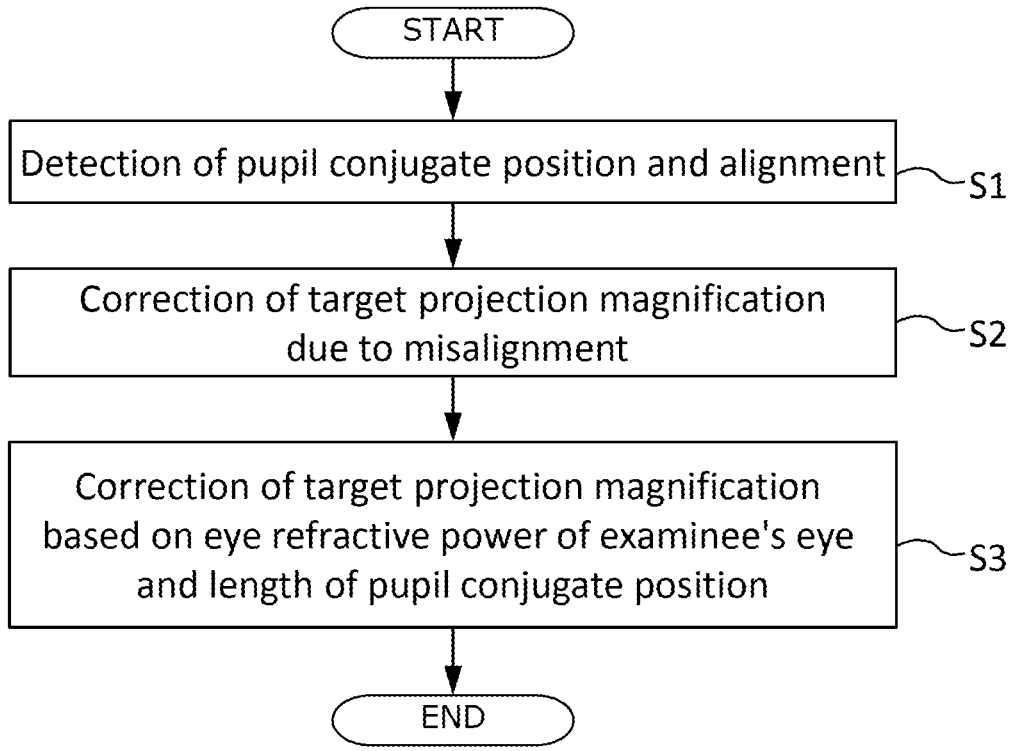
FIG. 7 is a flowchart illustrating a control operation.

For example, FIG. 7 is a flowchart illustrating a control operation in this example. Hereinafter, the description will be provided in an order based on the flowchart.

<Detection of Pupil Conjugate Position and Alignment (S1)>

For example, the objective eye refractive power (objective value) described above is used at the time of starting the subjective measurement, and thereby the calibration optical system 60 is controlled in association with the eye refractive power of the examinee's eye E. For example, the controller 70 moves the display 31 in the direction of the optical axis L2 based on the objective eye refractive power acquired by the objective measurement, thereby calibrating the eye refractive power of the examinee's eye E. For example, in a case where the eye refractive power of the examinee's eye E is −4.0 D (diopter), the controller 70 moves the display 31 in the direction of the optical axis L2 such that the eye refractive power of the examinee's eye E is calibrated to 0 D.

In addition, for example, the controller 70 may display a required target corresponding to a visual acuity value (for example, a target corresponding to a visual acuity value of 1.0) as an initial presentation target on the display 31. When the initial presentation target is presented to the examinee's eye E, the examiner performs a distance visual acuity measurement. For example, the examiner selects a predetermined switch on the monitor 4, thereby making it possible to switch targets corresponding to the visual acuity which are displayed on the display. For example, in a case where the examinee's answer is correct, the examiner switches the target to a target corresponding to a one-level higher visual acuity value. On the other hand, in a case where the examinee's answer is incorrect, the target is switched to a target corresponding to a one-level lower visual acuity value. In other words, the controller 70 may switch the target that is displayed on the display 31 based on a signal for a change of the visual acuity value from the monitor 4. In the example, the distance visual acuity measurement is exemplified and described; however, the measurement is not limited thereto. For example, it is possible to perform the near visual acuity measurement in the same manner as that in the distance visual acuity measurement.

For example, the examiner instructs the examinee to put the chin on the chin rest 5 so as to observe the presentation window 3 and to fixate the eye on the target. For example, when the anterior chamber of the examinee's eye E is detected by the anterior chamber imaging optical system 100, the controller 70 starts the position adjustment of the examinee's eye E and the measurement unit 7. That is, the controller 70 starts automatic alignment.

Figure 8:
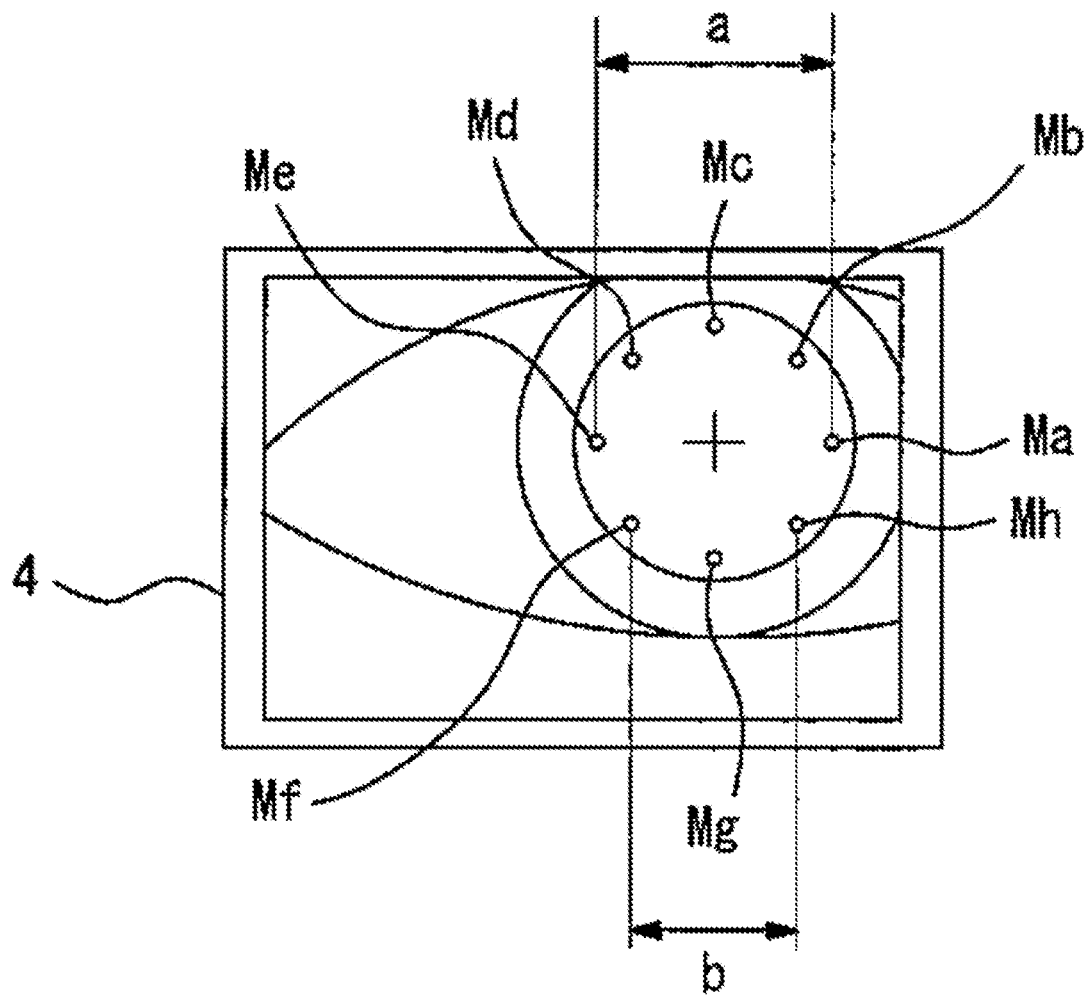
FIG. 8 is a view illustrating a pupil conjugate position in a measurement unit.

FIG. 8 is a view illustrating an anterior chamber image of the examinee's eye E. For example, when the alignment state is measured, the light sources provided in the first mark projecting optical system 45 and the second mark projecting optical system 46 are turned on. In this manner, mark images Ma to Mh are projected to have a ring shape to the examinee's eye E. For example, the controller 70 detects an XY central coordinate (cross mark in FIG. 8) in the mark images Ma to Mh, as a substantial cornea apex position. For example, the mark images Ma to Me represent infinite distances, and the mark images Mh to Mf represent finite distances. For example, in a case where the examinee's eye E is positioned at an appropriate operation length with respect to the subjective optometry apparatus 1 (that is, a case where the examinee's eye E is placed at a position Z1 to be described below), an image interval a between the mark images Ma and Me at the infinite distances and an image interval b between the mark images Mh and Mf at the finite distances are set at a constant ratio. For example, in this example, the appropriate operation length is obtained at a position at which a pupil position P of the examinee's eye E and a pupil conjugate position R of the light projecting optical system 30 are coincident with each other. In this example, a configuration of causing the pupil position P of the examinee's eye E and the pupil conjugate position R of the light projecting optical system 30 to be coincident with each other by using the operation length from a cornea apex position K of the examinee's eye E to the presentation window 3 of the subjective optometry apparatus 1.

For example, in a case where the examinee's eye E deviates in the Z direction and is not positioned at the appropriate operation length, the image interval between the mark images Ma and Me at the infinite distances little changes, but the image interval between the mark images Mh and Mf at the finite distances changes. For example, the controller 70 is capable of calculating a change in the operation length from the cornea apex position K of the examinee's eye E to the presentation window 3 of the subjective optometry apparatus 1 by comparing image ratios (that is, a/b) of the image interval a between the mark images Ma and Me at the infinite distances and the image interval b between the mark images Mh and Mf at the finite distances. For example, an amount of change in operation length is equal to a length Δg (refer to FIG. 9) of deviation of the cornea apex position K of the examinee's eye E in the Z direction. Regarding the details of the configuration described above, refer to JP-A-H06-46999.

In this example, a configuration of using the mark images at finite distances and infinite distances so as to identify the cornea apex position K on the examinee's eye E is exemplified and described; however, the configuration is not limited thereto. For example, the cornea apex position K of the examinee's eye E may be identified from an anterior chamber image of the examinee which is imaged by the anterior chamber imaging optical system 100 without using such mark images.

Figure 9:
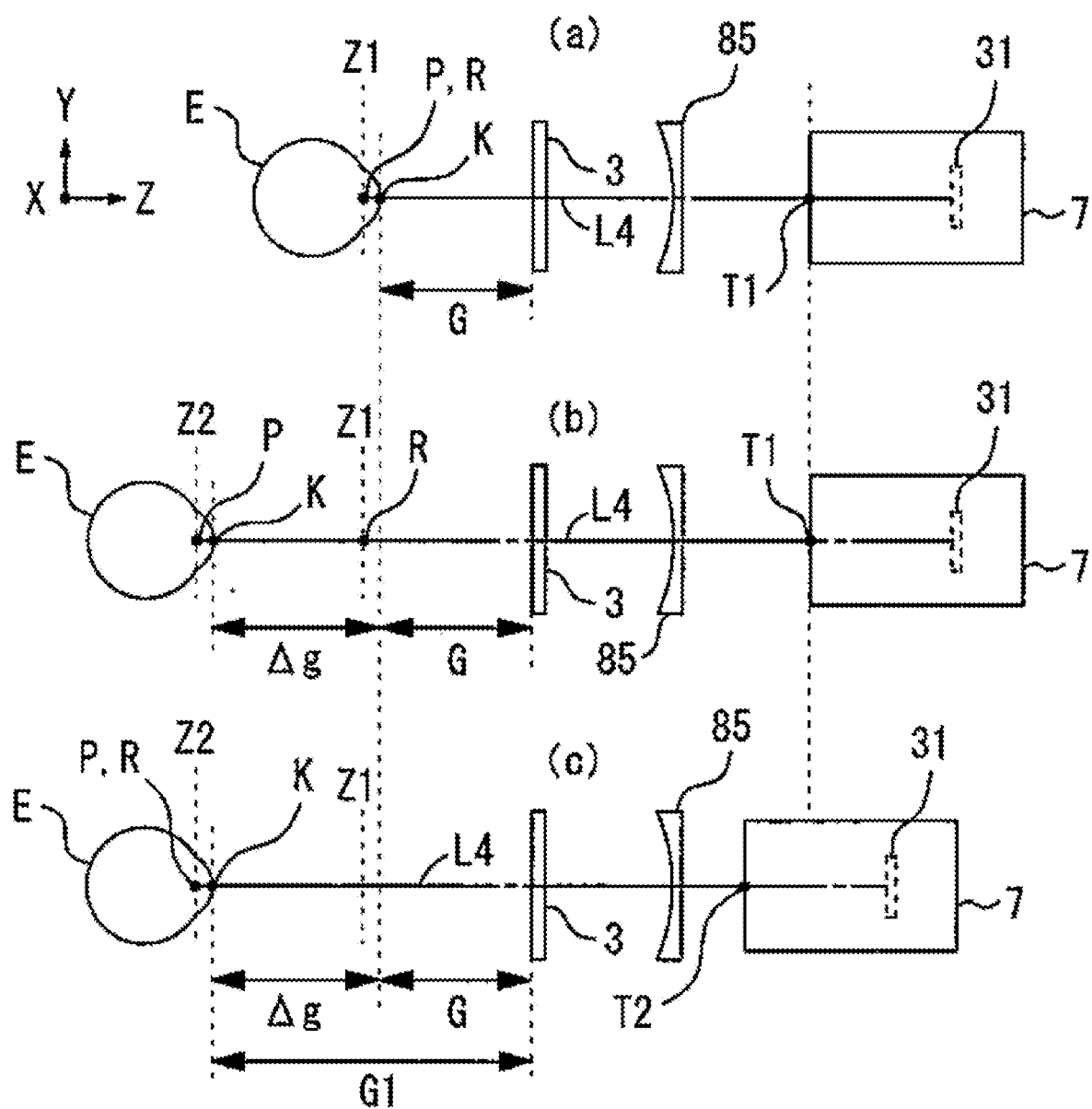
FIG. 9 is a view illustrating an anterior chamber image of an examinee's eye.

FIG. 9 is a view illustrating the pupil conjugate position R in the measurement unit 7. For example, (a) in FIG. 9 illustrates a case where there is no positional deviation between the examinee's eye E and the measurement unit 7. For example, (b) in FIG. 9 illustrates a case where the examinee's eye E deviates with respect to the measurement unit 7 in the Z direction. For example, (c) in FIG. 9 illustrates a case where the measurement unit 7 is moved and the position adjustment is performed in the case where the examinee's eye E deviates with respect to the measurement unit 7 in the Z direction. For convenience of description, FIG. 9 illustrates a simplified view in which the examinee's eye E, the presentation window 3, the concave mirror 85, and the measurement unit 7 are disposed on a straight line.

For example, the presentation window 3 and the concave mirror 85 are fixedly disposed in the subjective optometry apparatus 1. For example, in a case of performing the measurement, the position adjustment of the pupil position P of the examinee's eye E and the pupil conjugate position R (a position at which a width of a light flux diameter of the target is controlled in the light projecting optical system, that is, the pupil conjugate position R of the objective lens 14 on the side of the examinee in this example) which is present outside the subjective optometry apparatus 1 is performed. For example, in this example, the operation length is measured by using the first mark projecting optical system 45 and the second mark projecting optical system 46, and the alignment is adjusted. For example, in a state in which the first mark projecting optical system 45 and the second mark projecting optical system 46 are used, and the alignment is completed, the position adjustment of the pupil position P of the examinee's eye E and the pupil conjugate position R which is present outside the subjective optometry apparatus 1 is performed.

For example, in this example, the measurement unit 7 is moved in the Z direction by changing the positional relationship between the examinee's eye E and the measurement unit 7, and thereby it is possible to move the pupil conjugate position R in the Z direction and to perform the position adjustment of the pupil position P of the examinee's eye and the pupil conjugate position R. In addition, in this case, a configuration, in which another optical element (for example, the deflecting mirror 81) in the subjective optometry apparatus 1 is moved along with the measurement unit 7, may be employed. For example, the other optical element may be configured to integrally move with the measurement unit 7. In addition, for example, the other optical element and the measurement unit 7 may be configured to separately move from each other.

In this example, the operation length between the examinee's eye E and the presentation window 3 is measured by using the first mark projecting optical system 45 and the second mark projecting optical system 46, and the alignment state is adjusted; however, the example is not limited thereto. For example, an operation length between the examinee's eye and the other member of the subjective optometry apparatus 1 may be set as the operation length to be measured. For example, an operation length between the examinee's eye E and the measurement unit 7 may be set as the operation length to be measured. For example, an operation length between the examinee's eye E and the deflecting mirror 81 may be set as the operation length to be measured.

For example, in this example, a deviation amount in the operation length between the examinee's eye E and the presentation window 3 is equal to a deviation amount between the pupil position P of the examinee's eye E and the pupil conjugate position R of the light projecting optical system 30. In this example, to be equal includes meaning of to be substantially equal. In this example, the operation length between the examinee's eye E and the presentation window 3 is set as the operation length from the cornea apex position K of the examinee's eye E to the presentation window 3. For example, the pupil position P of the examinee's eye E is positioned on the rear side from the cornea apex position K by a predetermined length (for example, 3 mm), and thus it is possible to detect the pupil position P by detecting the cornea apex position K of the examinee's eye E.

For example, an amount of change (deviation amount) in operation length from the cornea apex position K of the examinee's eye E to the presentation window 3 of the subjective optometry apparatus 1 is equal to the length $\Delta g$ (refer to FIG. 9) of deviation of the cornea apex position K of the examinee's eye E in the Z direction. For example, the deviation amount of the operation length from the cornea apex position K of the examinee's eye E to the presentation window 3 of the subjective optometry apparatus 1 can be represented by G1-G (refer to (a) and (b) in FIG. 9). That is, for example, the deviation amount (G1-G) of the operation length is equal to the length $\Delta g$ of the deviation of the cornea apex position K of the examinee's eye E in the Z direction.

For example, the pupil position P of the examinee's eye E is positioned on the rear side from the cornea apex position K by the predetermined length (for example, 3 mm), and thus it is possible to consider that the deviation amount of the cornea apex position K of the examinee's eye E is equal to the deviation amount of the pupil position P. That is, in a case where the length of deviation of the cornea apex position K of the examinee's eye E in the Z direction is the length $\Delta g$, a length of deviation of the pupil position P in the Z direction is $\Delta g$.

For example, in FIG. 9, the pupil conjugate position R of the light projecting optical system 30 is set to a position of the position Z1, and the position of the measurement unit 7 is set as an initial position T1 in a case where the pupil position P of the examinee's eye in the emmetropia (the examinee's eye having the eye refractive power of 0 D) is coincident with the pupil conjugate position R. In addition, for example, the operation length obtained in a case where the pupil position P of the examinee's eye in the emmetropia (the examinee's eye having the eye refractive power of 0 D) is coincident with the pupil conjugate position R is set as the appropriate operation length G for performing the measurement.

For example, the state illustrated in (a) of FIG. 9 is a state in which the examinee's eye E is positioned at an appropriate length with respect to the presentation window 3 of the subjective optometry apparatus 1 (an alignment complete state), and the pupil position P of the examinee's eye E is coincident with the position Z1. Therefore, the pupil position P of the examinee's eye E is coincident with the pupil conjugate position R, and the examinee's eye E and the measurement unit 7 have an optically conjugate positional relationship via the concave mirror 85. For example, in this example, the position adjustment between the pupil position P and the pupil conjugate position R is performed as described above, and thereby a state in which it is possible to start the measurement is obtained.

For example, when the examinee puts the chin on the chin rest 5, the examinee's eye E is not positioned at the appropriate operation length, but the pupil position P of the examinee's eye E deviates with respect to the position Z1 in the frontward-rearward direction (Z direction) in some cases. For example, in (b) of FIG. 9, the pupil position P of the examinee's eye E deviates from the position Z1 to a position Z2 on a rear side by the length $\Delta g$. In this state, the examinee's eye E is not positioned at the appropriate operation length (the alignment is not completed), but the pupil position P of the examinee's eye E is not coincident with the pupil conjugate position R.

For example, the controller 70 moves the measurement unit 7 in the Z direction based on the operation length between the cornea apex position K of the examinee's eye E and the presentation window 3, and the alignment state is adjusted. That is, the position of the pupil conjugate position R is moved to the pupil position P of the examinee's eye E by moving the measurement unit 7 in the Z direction. For example, as illustrated in (c) of FIG. 9, the controller 70 moves the measurement unit 7 from the initial position T1 to a position T2.

For example, the controller 70 measures the operation length G1 between the cornea apex position K of the examinee's eye E and the presentation window 3 and moves the measurement unit 7 based on the measured operation length G1. In this case, for example, the controller 70 moves the measurement unit 7 based on a deviation amount of the measured operation length G1 and the preset appropriate operation length G (which is equal to the deviation amount Δg obtained in the case where the pupil position P of the examinee's eye E deviates from the position Z1 to the position Z2). In this manner, the position of the pupil conjugate position R moves to the pupil position P of the examinee's eye E. That is, the controller 70 measures the alignment state with respect to the examinee's eye E in an operation length direction (Z direction), thereby moving the measurement unit 7 with respect to the examinee's eye E in the optical axis direction.

More specifically, for example, the controller 70 moves the measurement unit 7 in a direction of an optical axis L4 based on the length Δg of the deviation of the examinee's eye E from the position Z1 to the position Z2 in the Z direction (the amount of change in operation length from the cornea apex position K of the examinee's eye E to the presentation window 3) (refer to FIG. 9). For example, in this example, the measurement unit 7 is integrally moved with the concave mirror 85 in the direction of the optical axis L4, and thereby it is possible to change the length from the pupil position P of the examinee's eye E to the pupil conjugate position R. In this manner, the pupil conjugate position R of the light projecting optical system 30 moves in the direction of the optical axis L4.

For example, the controller 70 measures the alignment state in the Z direction as described above (for example, the operation length) and adjusts the position of the measurement unit 7 based on the measurement result, and thereby it is possible to dispose the pupil conjugate position R with respect to the examinee's eye E that is positioned at the position Z2. That is, the examinee's eye E that is positioned at the position Z2 and the measurement unit 7 have an optically conjugate positional relationship, and the alignment of the measurement unit 7 with respect to the examinee's eye E at the position Z2 is completed.

<Correction for Target Projection Magnification Due to Misalignment (S2)>

Here, for example, when the position of the measurement unit 7 is adjusted with respect to the examinee's eye E, the pupil conjugate position R moves, and thus a projection magnification of the target that is projected to the examinee's eye E changes. Therefore, for example, the controller 70 acquires positional information of the measurement unit 7.

For example, a movement amount of the measurement unit 7 or the positional coordinate of the measurement unit 7 may be acquired as the positional information of the measurement unit 7. In addition, for example, relative positional information of the concave mirror 85 and the measurement unit 7 or relative positional information of the examinee's eye E and the measurement unit 7 may be acquired as the positional information of the measurement unit 7. For example, in this case, the controller 70 acquires relative positional information of the measurement unit 7 and the concave mirror 85 or the examinee's eye E. For example, such relative positional information may be acquired by detecting both of the position of the concave mirror 85 or the examinee's eye E and the position of the measurement unit 7 by the controller 70.

For example, a configuration of acquiring the positional information of the measurement unit 7 by using positional information changed by the adjustment of the position of the entire measurement unit 7 may be employed. In addition, for example, a configuration of acquiring the positional information of the measurement unit 7 by using positional information changed by the adjustment of the position of at least one member (for example, a lens or a display) of the light projecting optical system 30 provided in the measurement unit 7 may be employed.

Figure 10:
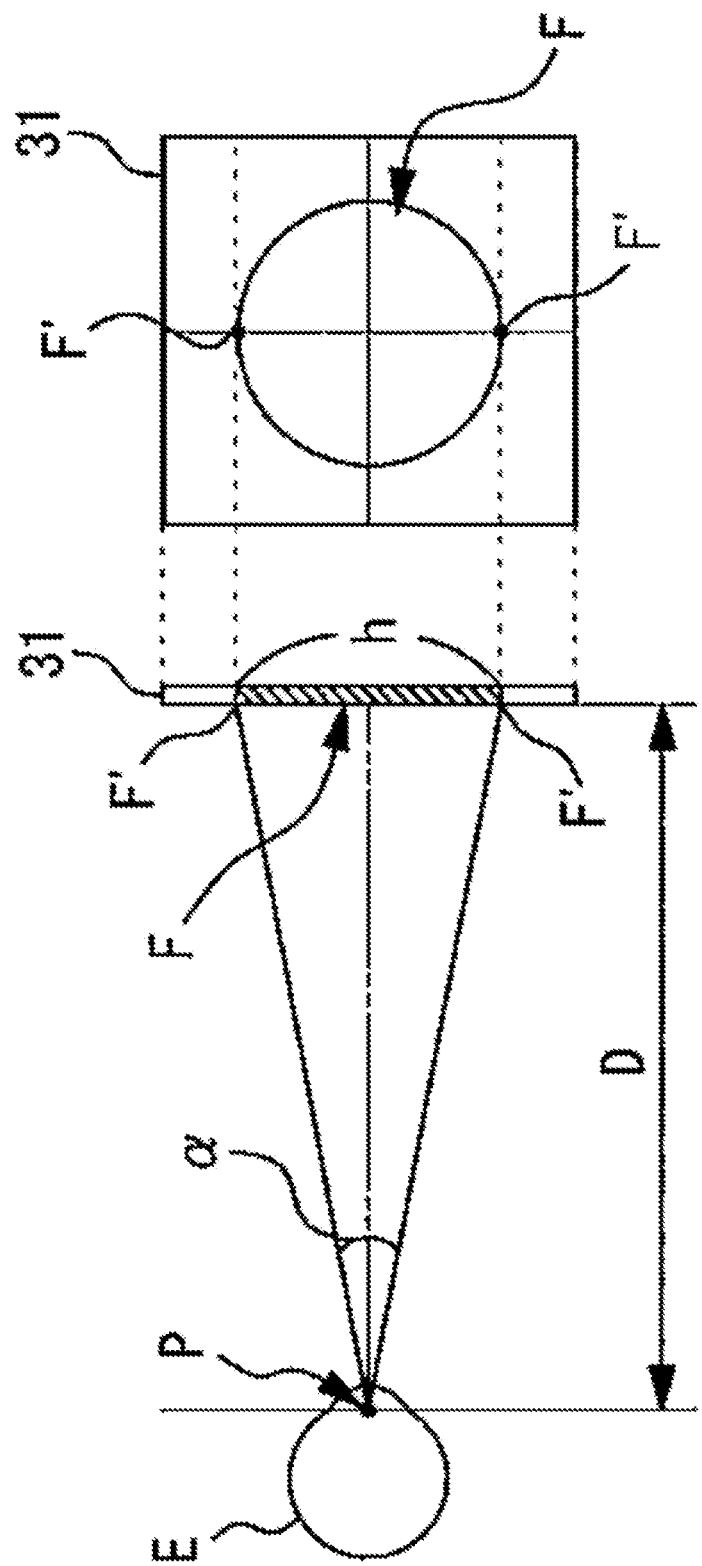
FIG. 10 is a view illustrating a vision angle of the examinee's eye.

For example, the controller 70 may be configured to calculate the projection magnification of the target light flux that is projected to the examinee's eye E by acquiring the positional information of the measurement unit 7. Hereinafter, a change in projection magnification of the target light flux will be described. For example, the change in projection magnification of the target light flux is influenced by a vision angle α of the examinee's eye E. FIG. 10 is a view illustrating a vision angle α of the examinee's eye E.

For example, when the examinee's eye E is fixated on a target F (hatched portion) that is displayed on the display 31, both ends F' of the target F are reflected in a peripheral visual field of the examinee's eye E. The target F has both ends in both of the upward-downward direction and the rightward-leftward direction; however, in this example, for convenience, only both ends F' of the target F in the upward-downward direction are illustrated and described. For example, the vision angle α of the examinee's eye E is represented by an angle made between two lines obtained by connecting the pupil position P of the examinee's eye E and both ends F' of the target F. That is, the vision angle α is represented as an angle at which the target F is viewed by the examinee's eye E.

For example, it is possible to express the vision angle α in equation (1) established by using a length D from the pupil position P of the examinee's eye E to the target F and a size h of the target F.

$$\alpha/2 = \tan^{-1}(h/2D) \quad (1)$$

For example, according to equation (1), the shorter the length D from the pupil position P of the examinee's eye E to the target F, the larger the vision angle α. In addition, as the vision angle α increases, the size h of the target F is viewed to be larger to the examinee's eye E. On the other hand, the longer the length D from the pupil position P of the examinee's eye E to the target F, the smaller the vision angle α. In addition, as the vision angle α decreases, the size h of the target F is viewed to be smaller to the examinee's eye E. When the vision angle α is the same, the target F is viewed to have the same size to the examinee's eye E even when the length D from the pupil position P of the examinee's eye E to the target F changes.

For example, such a vision angle α of the examinee's eye E changes due to the alignment state of the measurement unit 7 with respect to the examinee's eye E. In other words, the size of the vision angle α changes by adjusting the position of the measurement unit 7 with respect to the concave mirror 85 and moving the pupil conjugate position R.

Figure 11:
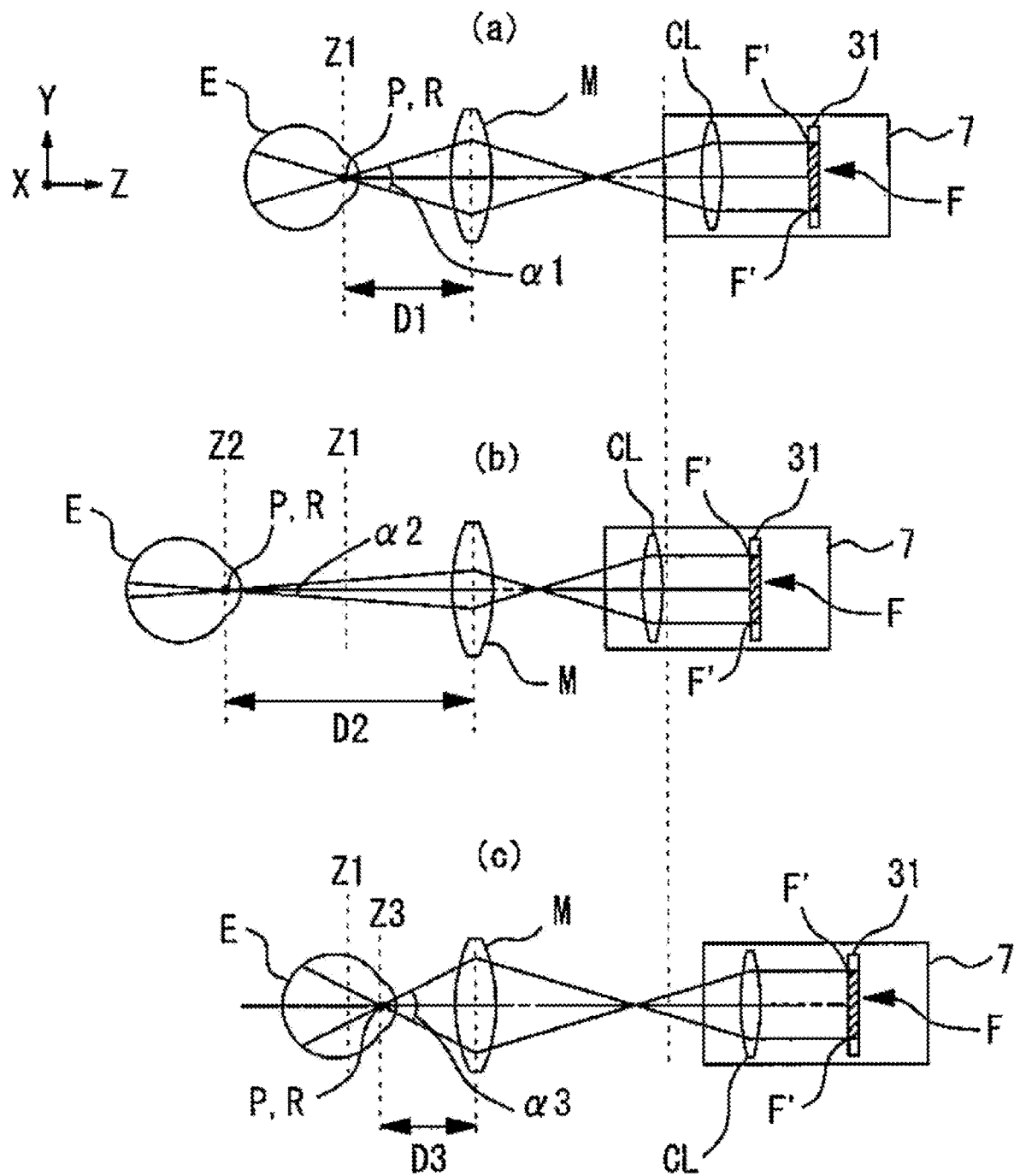
FIG. 11 is a view illustrating a change in vision angle due to alignment.

For example, FIG. 11 is a view illustrating the change in vision angle α due to the alignment. (a) in FIG. 11 illustrates a state in which the examinee's eye E is placed at the position Z1 (refer to FIG. 8). (b) in FIG. 11 illustrates a state in which the examinee's eye E is placed at the position Z2 on the rear side (that is, a separate direction from the concave mirror 85) from the position Z1. (c) in FIG. 11 illustrates a state in which the examinee's eye E is placed at a position Z3 on the front side (that is, an approach direction to the concave mirror 85) from the position Z1. For convenience of description, in FIG. 11, the deflecting mirror 81 is omitted, the objective lens 14, the projection lens 33, and the projection lens 34 which are provided in the measurement unit 7 are replaced with a convex lens CL and the description thereof is provided. In addition, since the concave mirror 85 can be considered to be the same even in the convex lens in this example, the concave mirror 85 is replaced with a convex lens M in FIG. 11, and the description thereof is provided. For example, in FIG. 11, even when the examinee's eye E is positioned at any position of the position Z1 ((a) of FIG. 11), the position Z2 ((b) of FIG. 11), or the position Z3 ((c) of FIG. 11), the position of the measurement unit 7 is adjusted with respect to the examinee's eye E. and the position adjustment of the pupil position P of the examinee's eye E and the pupil conjugate position R is performed.

For example, in FIG. 11, the target light flux from the display 31 is projected in a parallel manner. That is, the target light flux that is emitted from the display 31 proceeds forward to the position of the convex lens CL in a parallel manner. For example, the target light flux is refracted by the convex lens CL, then, is further refracted by the fixedly disposed concave mirror 85 (the convex lens M in FIG. 11), and is incident to the examinee's eye E. Therefore, the position of the convex lens M can substantially considered as the position at which the display 31 is disposed. That is, the length D (refer to FIG. 10) from the pupil position P of the examinee's eye E to the target F can be considered as a length from the pupil position P of the examinee's eye E to the convex lens M.

For example, as illustrated in (a) of FIG. 11, the target light flux from both ends F' of the target F is incident to the pupil position P of the examinee's eye E via the convex lens CL and the convex lens M. For example, in this state, the length from the pupil position P to the target F (the length from the pupil position P to the convex lens M) is a length D1. In addition, for example, a vision angle α1 of the examinee's eye E is represented by an angle made between the pupil position P of the examinee's eye E and target light fluxes refracted by the convex lens M.

For example, in a state in which the examinee's eye E is positioned at the position Z2 or Z3, the vision angle α at which the target F that is displayed on the display 31 is viewed by the examinee's eye E changes when the measurement unit 7 moves so as to cause the pupil conjugate position R to be coincident with the pupil position P of the examinee's eye E.

For example, as illustrated in (b) of FIG. 11, in a state in which the examinee's eye E is positioned at the position Z2 on the rear side from the position Z1, a length D2 from the pupil position P of the examinee's eye E to the convex lens M becomes longer than the length D1. Therefore, a vision angle α2 at which the target F is viewed by the examinee's eye E via the convex lens M and the convex lens CL becomes narrower (smaller) than the vision angle α1 made in a state in which the examinee's eye E is placed at the position Z1. For example, at this time, a relationship of vision angle α1>vision angle α2 of the examinee's eye E is established, and thus the size h of the target F is viewed to be smaller in a case where the target F is viewed by the examinee's eye E from the position Z2, compared to when the target F is viewed by the examinee's eye E from the position Z1.

In addition, for example, as illustrated in (c) of FIG. 11, in a state in which the examinee's eye E is positioned at the position Z3 on the front side from the position Z1, a length D3 from the pupil position P of the examinee's eye E to the convex lens M becomes shorter than the length D1. Therefore, a vision angle α3 at which the target F is viewed by the examinee's eye E via the convex lens M and the convex lens CL becomes broader (larger) than the vision angle α1 made in a state in which the examinee's eye E is placed at the specified position Z1. For example, at this time, a relationship of vision angle α1<vision angle α3 of the examinee's eye E is established, and thus the size h of the target F is viewed to be larger in a case where the target F is viewed by the examinee's eye E from the measurement position Z3, compared to when the target F is viewed by the examinee's eye E from the specified position Z1.

For example, as described above, in a case where the examinee's eye E deviates from the position Z1, the size of the vision angle α changes according to the alignment completion with respect to the examinee's eye E in the Z direction. Therefore, in a state in which the examinee's eye E is placed at the position Z1 and in a state in which the examinee's eye E is placed at the position Z2 or Z3, the target light fluxes are not projected from the target F toward the examinee's eye E at the equal projection magnification. For example, in a case of detecting that the pupil position P of the examinee's eye E deviates from the position Z1 (the measurement unit 7 moves from the initial position T1), the controller 70 performs the alignment in the Z direction and corrects the projection magnification of the target light flux that is projected to the examinee's eye E.

For example, the controller 70 sets a correction amount for correcting the projection magnification of the target light flux that is projected to the examinee's eye E, based on the relative positional information of the concave mirror 85 and the measurement unit 7. For example, the relative positional information of the concave mirror 85 and the measurement unit 7 may be calculated by using the length Δg of the deviation of the examinee's eye E from the position Z1 in the Z direction. For example, in a case of performing the alignment in the Z direction, the measurement unit 7 is moved with respect to the concave mirror 85 based on the length Δg (refer to FIG. 9) of the deviation of the examinee's eye E from the position Z1 in the Z direction. That is, it is possible to acquire the relative positional information of the concave mirror 85 and the measurement unit 7 based on the length Δg.

For example, the memory 75 stores a correction table for performing conversion into a correction amount for correcting the projection magnification of the target light flux that is projected to the examinee's eye E, based on the relative positional information of the concave mirror 85 and the measurement unit 7. For example, such a correction table may be set by performing experiments or simulations in advance. For example, the controller 70 acquires the relative positional information of the concave mirror 85 and the measurement unit 7 and, then, acquires the correction amount for correcting the projection magnification of the target light flux from the correction table. For example, the correction amount is set such that the projection magnification of the target light flux that is projected to the examinee's eye E is 1.0. For example, the subjective optometry apparatus 1 in this example has a configuration in which, in a case where the measurement unit 7 is positioned at the initial position T1 (a case where the pupil conjugate position R is positioned at the position Z1), the projection magnification of the target light flux that is projected to the examinee's eye E is 1.0.

For example, hereinafter, a state in which the examinee's eye E is separated from the position Z1 to the rear side by 10 mm will be exemplified and described. For example, the controller 70 measures the length Δg of the deviation of the examinee's eye E from the position Z1 by using the mark images Ma to Mh described above. In this manner, for example, the controller detects that the length Δg is 10 mm. Subsequently, the controller 70 performs the alignment with respect to the examinee's eye E in the Z direction, moves the pupil conjugate position R of the measurement unit 7, and causes the pupil conjugate position R to be coincident with the pupil position P of the examinee's eye E. For example, the measurement unit 7 moves with respect to the concave mirror 85 by 10 mm, and thereby the alignment in the Z direction (position adjustment of the pupil conjugate position R and the pupil position P) is completed.

For example, when completing the alignment, the controller 70 acquires 10 mm as the relative positional information of the concave mirror 85 and the measurement unit 7 (for example, the movement amount of the measurement unit 7). For example, the controller 70 sets a correction amount of the projection magnification, based on the relative positional information of the concave mirror 85 and the measurement unit 7. For example, regarding the projection magnifications of the target light flux, the correction amounts by which the projection magnification of the target light flux is set to 1.0 are stored as the correction table according to the relative positional information of the concave mirror 85 and the measurement unit 7. For example, a reciprocal of the projection magnification may be set as such a correction amount. For example, in a case where the length Δg is 10 mm on the rear side from the position Z1 (a state in which the measurement unit 7 moves to the rear side by 10 mm), the projection magnification of the target light flux is 0.975, and thus the correction amount of about 1.026 is acquired. For example, the controller 70 is capable of acquiring and setting the correction amount for correcting the projection magnification of the target light flux from the relative positional information of the concave mirror 85 and the measurement unit 7 by using the correction table.

Subsequently, the controller 70 corrects the projection magnification of the target light flux based on the correction amount described above. For example, the controller 70 changes the size of the target F that is displayed on the display 31, based on the set correction amount, in order to project the target light flux to the examinee's eye E at the projection magnification of 1.0. For example, the controller 70 in this example is capable of changing the size of the target F by changing the number of pixels of the target F that is displayed on the display 31.

For example, in a state in which the examinee's eye E is positioned at the position Z1, the target light flux is projected to the examinee's eye E such that the projection magnification of the target F is 1.0. For example, at this time, the target F having 100 pixels is displayed on the display 31. For example, in a case where the examinee's eye E deviates from the position Z1 in the Z direction, and the correction amount is set to 1.026, the controller 70 changes the size of the target F 1.026 times and displays the target F having about 103 pixels on the display 31. For example, the controller 70 controls target display on the display 31 as described above, and thereby the projection magnification of the target light flux that is projected toward the examinee's eye E is corrected to 1.0.

For example, the alignment in the Z direction is performed with respect to the examinee's eye E as described above, the projection magnification of the target light flux that is projected to the examinee's eye E is corrected, and then the subjective measurement of the examinee's eye E is started by using the subjective measurement optical system.

<Correction for Target Projection Magnification Based on Eye Refractive Power of Examinee's Eye and Length of Pupil Conjugate Position (S3)>

For example, the display 31 provided in the light projecting optical system 30 is disposed at a standby position at which the target light flux (target light flux of 0 D) without calibration performed on the examinee's eye E is projected in a case where the measurement unit 7 is disposed at the initial position T1. That is, for example, the standby position of the display 31 is a synthetic focal position f (refer to FIG. 12) of the objective lens 14, the projection lens 33, and the projection lens 34 with respect to the examinee's eye E having the eye refractive power of 0 D.

For example, when the subjective measurement is started, as described above, the objective eye refractive power is used, and thereby the calibration optical system 60 is controlled in association with the eye refractive power of the examinee's eye. For example, the controller 70 moves the display 31 in the direction of the optical axis L2 and disposes the display at an initial position e (refer to FIG. 12) used when performing the subjective measurement based on at least one of objectively measured refractive powers such as the spherical refractivity S, the cylindrical reflectivity C, the astigmatic axis angle A, and the prism amount Δ of the examinee's eye E.

For example, the initial position e of the display 31 changes depending on the eye refractive power of the examinee's eye E. In other words, the display 31 moves from the standby position to the initial position e different from the standby position for the examinee's eye E having an eye refractive power that is not 0 D. For example, the display 31 does not move from the standby position, and the standby position is set as the initial position e for the examinee's eye E having the eye refractive power of 0 D. In this manner, for example, the controller 70 is capable of acquiring the calibration power of the calibration optical system 60. That is, the controller 70 is capable of acquiring, from the disposed position of the display 31, the calibration power for calibrating the examinee's eye E such that the examinee's eye has the eye refractive power of 0 D.

For example, when the position of the display 31 is moved, the subjective measurement is started. For example, after the subjective measurement is started, the examinee's eye E cannot be maintained in a fixated state on the target during the subjective measurement but slightly moves, and thus fixation deviation occurs in some cases. In addition, the position of the face of the examinee is likely to move, and thus fixation deviation occurs in some cases.

For example, in this case, the projection magnification of the target light flux changes in some cases. For example, when the display 31 is disposed at the initial position e different from the standby position (a case where the examinee's eye is the examinee's eye that does not have the refractive power of 0 D), and further the examinee's eye E slightly moves from a position at which the alignment is completed (for example, the position Z2 in FIG. 9) in the frontward-rearward direction (Z direction) (the pupil position P of the examinee's eye E and the pupil conjugate position R of the light projecting optical system 30 deviate), the vision angle α, at which the target F is viewed by the examinee's eye E, changes. In this manner, the projection magnification of the target light flux that is projected to the examinee's eye E changes. For example, in a case where the display 31 is disposed at the standby position (a case where the examinee's eye is the examinee's eye E having the refractive power of 0 D), and the examinee's eye E slightly moves in the frontward-rearward direction (Z direction) from the position at which the alignment is completed, the vision angle α does not change.

Figure 12:
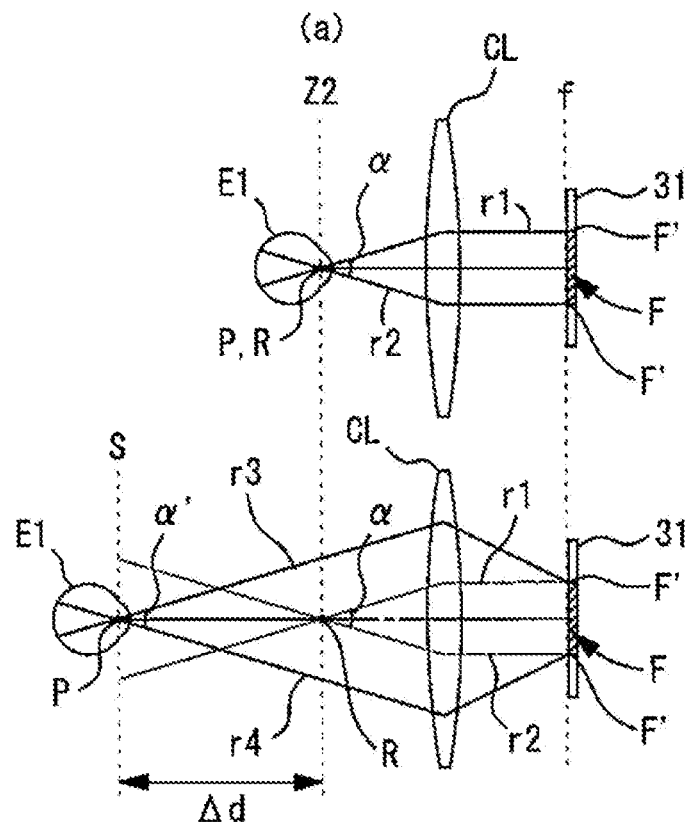
FIG. 12 is a view illustrating a change in vision angle depending on the eye refractive power of the examinee's eye.
Figure 12:
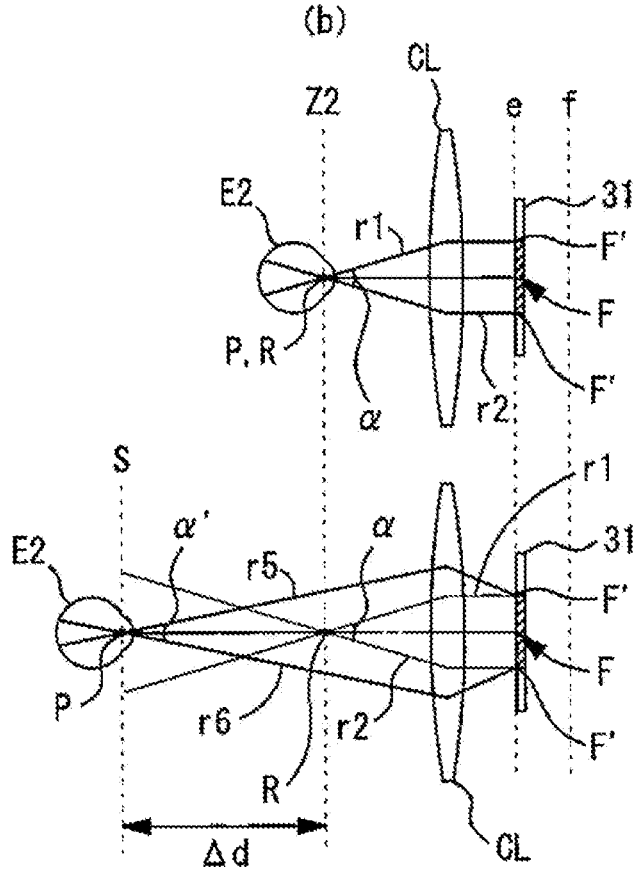

Hereinafter, a relationship between the length between the examinee's eye E and the pupil conjugate position R, the eye refractive power of the examinee's eye E, and the vision angle α will be described. For example, FIG. 12 is a view illustrating a change in vision angle α depending on the eye refractive power of the examinee's eye E. (a) in FIG. 12 illustrates a case where the eye refractive power of the examinee's eye E is 0 D. (b) in FIG. 12 illustrates a case where the eye refractive power of the examinee's eye E is not 0 D. For example, in this example, a case where the examinee's eye E has myopia (for example, a case where the eye has the refractive power of −10 D) is exemplified as a case where the eye refractive power is not 0 D. For example, for convenience of description, in FIG. 12, the objective lens 14, the projection lens 33, and the projection lens 34 which are provided in the measurement unit 7 are replaced with one convex lens CL and the description thereof is provided.

For example, in a case of an examinee's eye E1 having the eye refractive power of 0 D (that is, a state illustrated in (a) of FIG. 12), the display 31 is disposed at the standby position. That is, for example, the display 31 is disposed at the synthetic focal position f (a focal position f of the convex lens CL in FIG. 12) of the objective lens 14, the projection lens 33, and the projection lens 34.

For example, the display 31 emits the target light flux in various directions. For example, in a case where the examinee's eye E1 is placed at the position Z2 (the alignment completion position (position at which the pupil position P is coincident with the pupil conjugate position R)), parallel target light fluxes r1 and r2, which radiate from both ends F' of the target F, are incident to the examinee's eye E1 by being refracted from the convex lens CL. At this time, the angle α of the examinee's eye E1 positioned at the position Z2 can be represented by an angle made between the pupil position P of the examinee's eye E and the target light fluxes r1 and r2.

For example, when the examinee's eye E1 is placed at a position S by slightly moving in the Z direction (hereinafter, slight moving position S), the target light flux that is incident to the pupil position P of the examinee's eye E1 changes. For example, the parallel target light fluxes r1 and r2, which radiate from the display 31, are not incident to the pupil position P of the examinee's eye E1 at the slight moving position S. For example, in this state, among the target light fluxes radiating from the display 31 in various directions, target light fluxes r3 and r4 are refracted from the convex lens CL, thereby being incident to the pupil position P of the examinee's eye E1. At this time, an angle α' of the examinee's eye E1 at the slight moving position S can be represented by an angle made between the pupil position P of the examinee's eye E and the target light fluxes r3 and r4.

For example, since the target light flux r1 and the target light flux r3 have the same focal position f with respect to the convex lens CL, the target light flux r1 and the target light flux r3 are the target light fluxes that are incident to the examinee's eye E at angles parallel to each other via the convex lens CL. Similarly, since the target light flux r2 and the target light flux r4 have the same focal position f with respect to the convex lens CL, the target light flux r2 and the target light flux r4 are the target light fluxes that are incident to the examinee's eye E at angles parallel to each other via the convex lens CL. Therefore, the vision angle α of the examinee's eye E1 is equal to the vision angle α'. In other words, regarding the examinee's eye E1 having the eye refractive power of 0 D, even when the display 31 is disposed at the standby position and the examinee's eye E1 slightly moves from the position Z2 in the Z direction, the projection magnification of the target light flux that is projected to the examinee's eye E1 does not change.

For example, in a case of an examinee's eye E2 having the myopia (that is, a state illustrated in (b) of FIG. 12), the display 31 is disposed at the initial position e different from the standby position. That is, since the examinee's eye E2 has a focal point on the nearer side that that of the examinee's eye E1 having the power of 0 D, the display 31 is disposed on the nearer side than the focal position f of the convex lens CL depending on the eye refractive power of the examinee's eye E2.

For example, in a case where the examinee's eye E2 is placed at the position Z2 (the alignment completion position (position at which the pupil position P is coincident with the pupil conjugate position R)), parallel target light fluxes r1 and r2, which radiate from both ends F' of the target F, are incident to the examinee's eye E2 by being refracted from the convex lens CL. At this time, the angle α of the examinee's eye E2 positioned at the measurement position Z2 can be represented by an angle made between the pupil position P of the examinee's eye E and the target light fluxes r1 and r2.

For example, when the examinee's eye E2 is placed at the slight moving position S, the target light flux that is incident to the pupil position P of the examinee's eye E2 changes. For example, the parallel target light fluxes r1 and r2, which radiate from the display 31, are not incident to the pupil position P of the examinee's eye E2 at the slight moving position S. For example, in this state, among the target light fluxes radiating from the display 31 in various directions, target light fluxes r5 and r6 are refracted from the convex lens CL, thereby being incident to the pupil position P of the examinee's eye E2. For example, since the disposed position of the display 31 is closer to the convex lens CL than the focal position f with respect to the examinee's eye E2, the target light fluxes r5 and r6 are incident to the examinee's eye E2 as diffused target light fluxes. At this time, the angle α' of the examinee's eye E2 at the slight moving position S can be represented by an angle made between the pupil position P of the examinee's eye E and the target light fluxes r5 and r6.

For example, since the target light flux r5 and the target light flux r6 are the diffused target light fluxes, the target light flux r1 and the target light flux r5 are not the target light fluxes that are incident to the examinee's eye E at angles parallel to each other via the convex lens CL. Similarly, since the target light flux r5 and the target light flux r6 are the diffused target light fluxes, the target light flux r2 and the target light flux r6 are not the target light fluxes that are incident to the examinee's eye E at angles parallel to each other via the convex lens CL. For example, as described above, regarding the examinee's eye E2 having the myopia, the size of the vision angle α' changes with respect to the vision angle α. In other words, regarding the examinee's eye E2 having the myopia, when the examinee's eye E2 slightly moves from the position Z2 in the Z direction, the projection magnification of the target light flux that is projected to the examinee's eye E2 changes. The size of such an angle α' changes as an absolute value of the eye refractive power of the examinee's eye E increases. Therefore, in a case where the examinee's eye E having a large absolute value of the eye refractive power slightly moves, it is necessary to correct the projection magnification of the target light flux to be higher, compared to a case where the examinee's eye E having small absolute value of the eye refractive power slightly moves.

Hereinafter, the projection magnification correction of the target light flux based on the length between the examinee's eye E and the pupil conjugate position R and the calibration power of the calibration optical system 60 based on the eye refractive power of the examinee's eye E will be described. For example, in this example, the controller 70 detects the length between the examinee's eye E (the pupil position P of the examinee's eye E in this example) and the pupil conjugate position R of the light projecting optical system 30. For example, in this example, the length between the examinee's eye E and the pupil conjugate position R of the light projecting optical system 30 may be obtained by using the amount of change in operation length. That is, the length between the examinee's eye E and the pupil conjugate position R of the light projecting optical system 30 may be obtained by measuring the alignment state.

For example, the controller 70 sets the correction amount for correcting the projection magnification of the target light flux that is projected to the examinee's eye, based on the measurement result described above and the calibration power of the calibration optical system 60 based on the eye refractive power of the examinee's eye E. That is, for example, the controller 70 sets the correction amount for correcting the projection magnification of the target light flux that is projected to the examinee's eye, based on the measurement result and the position of the display 31 moving based on the eye refractive power of the examinee's eye E. For example, the controller 70 corrects the projection magnification of the target light flux based on the set correction amount.

For example, the length between the examinee's eye E and the pupil conjugate position R of the light projecting optical system 30 is measured by measuring the alignment state of the examinee's eye E in an operation length direction (Z direction). For example, the controller 70 detects the alignment state of the examinee's eye E the operation length direction (Z direction). It is possible to determine the alignment state by comparing the image ratios (that is, a/b) of the image interval a between the mark images Ma and Me at the infinite distances and the image interval b between the mark images Mh and Mf at the finite distances as described above (refer to FIG. 8). For example, the controller 70 detects a length Δd from the position Z2 of the examinee's eye E (alignment completion position) to the slight moving position S of the examinee's eye E that slightly moves in the Z direction. That is, the controller 70 is capable of acquiring the length Δd as a length between the examinee's eye E and the pupil conjugate position R of the light projecting optical system 30 by using the amount of change in operation length (deviation amount of the alignment) from the examinee's eye E to the presentation window 3.

For example, when measuring the length between the examinee's eye E and the pupil conjugate position R of the light projecting optical system 30, the controller 70 sets the correction amount for correcting the projection magnification of the target light flux that is projected to the examinee's eye E, based on the measurement result thereof and the calibration power of the calibration optical system 60. For example, the memory 75 provided in the controller 70 stores the correction table for performing conversion into the correction amount for correcting the projection magnification of the target light flux that is projected to the examinee's eye E, based on the calibration power and the length Δd. For example, such a correction table may be set in advance for each of the calibration powers and the lengths Δd by performing experiments or simulations. For example, the controller 70 acquires the correction amount corresponding to the calibration power and the length Δd based on the correction table. For example, the correction amount is set such that the projection magnification of the target light flux that is projected to the examinee's eye E is 1.0.

For example, when acquiring the correction amount for causing the projection magnification of the target light flux that is projected to the examinee's eye E to be 1.0, the controller 70 adjusts the size of the target F by changing the number of pixels as described above. In this manner, the controller 70 is capable of causing the projection magnification of the target light flux that is projected toward the examinee's eye E to be corrected to 1.0.

As described above, for example, the subjective optometry apparatus in this example includes the acquiring portion that acquires the calibration power of the calibration optical system, the detection portion that detects the length between the examinee's eye and the pupil conjugate position of the light projecting optical system, the correction amount setting portion that sets the correction amount for correcting the projection magnification of the target light flux that is projected to the examinee's eye, and the correction portion that corrects the projection magnification of the target light flux. In this manner, the examiner can reduce a change in size of the target due to the deviation of the examinee's eye from the pupil conjugate position and the eye refractive power of the examinee's eye so as to subjectively measure the optical characteristics of the examinee's eye. Therefore, the examiner can perform subjective measurement with accuracy.

In addition, for example, in a case where the position of the examinee's eye moves or the like, it is difficult to perform the position adjustment of the pupil conjugate position of the light projecting optical system with respect to the examinee's eye. Even in this case, it is possible to present the target in the same size as the size of the target that can be observed when the position adjustment of the examinee's eye to the pupil conjugate position is performed. In this manner, when the position of the examinee's eye deviates, the size of the target is likely to change, and thus it is possible to suppress a state in which the examinee is difficult to observe the target. That is, the examiner can perform subjective measurement with accuracy.

In addition, for example, the subjective optometry apparatus in this example includes the measurement unit that accommodates the light projecting optical system, the acquiring portion that acquires the positional information of the measurement unit, the correction amount setting portion that sets the correction amount for correcting the projection magnification of the target light flux that is projected to the examinee's eye, and the correction portion that corrects the projection magnification of the target light flux. In this manner, in the subjective optometry apparatus including the fixed optical element, when adjusting the deviation between the examinee's eye and the pupil conjugate position of the light projecting optical system, the examiner can project the target having the same size to the examinee's eye even in a case where the projection magnification of the target that is projected to the examinee's eye is changed. Therefore, the examiner can perform subjective measurement on the examinee's eye with accuracy.

In addition, for example, the subjective optometry apparatus in this example includes the detection portion that detects the length between the examinee's eye and the pupil conjugate position of the light projecting optical system, and the adjustment portion that adjusts the position of the measurement unit in the optical axis direction, based on the detection result by the detection portion. In this manner, in a case where the position of the examinee's eye deviates, the length between the fixed optical element and the measurement unit is automatically adjusted such that the pupil conjugate position of the light projecting optical system is coincident with the examinee's eye. Therefore, the examiner can easily align the measurement unit with the examinee's eye.

In addition, for example, the subjective optometry apparatus in this example changes the size of the target that is displayed on the display, based on the set correction amount. In this manner, the examiner can easily correct the projection magnification of the target light flux.

In this case, for example, the subjective optometry apparatus in this example includes the optical element that is movable in the optical path of the light projecting optical system and the drive portion that moves the optical element along the optical path of the light projecting optical system. In addition, for example, the subjective optometry apparatus in this example is capable of moving the optical element based on the correction amount. Therefore, the examiner can dispose the optical element at an appropriate position with respect to the examinee's eye and correct the projection magnification of the target light flux with accuracy.

In addition, for example, the subjective optometry apparatus in this example is capable of presenting the target at the optically predetermined examination length in the subjective examination portion by using the concave mirror, and thus there is no need to dispose a member or the like such that the predetermined examination length becomes an actual length when the target is presented at the predetermined examination length. In this manner, there is no need to provide an extra member and a space, and thus it is possible to reduce the apparatus in size.

Modification Example

In this example, a configuration, in which the alignment of the examinee's eye E and the measurement unit 7 is automatically performed by the controller 70, is exemplified and described; however, the configuration is not limited thereto. For example, the alignment of the examinee's eye E and the measurement unit 7 may be manually performed by the examiner. For example, in this case, a configuration provided with a configuration that is capable of manually moving the measurement unit 7 is exemplified.

In this example, the correction amount is set such that the projection magnification of the target light flux is 1.0; however, the example is not limited thereto. It is needless to say that the projection magnification of the target light flux may be set to a value other than 1.0. For example, even in such a case, it is possible to correct the projection magnification of the target light flux toward the examinee's eye E in the same manner described above.

In this example, the configuration in which the correction amount is set such that the projection magnification of the target light flux is 1.0 is exemplified and described; however, the example is not limited thereto. For example, the correction amount may be set as a value of the vision angle $\alpha$ of the target light flux that is projected toward the examinee's eye E. For example, in this case, a configuration, in which the correction amount is set such that the vision angle $\alpha$ that changes by the movement of the examinee's eye E in the Z direction is coincident with the vision angle $\alpha$ at which the target F is viewed by the examinee's eye E at the position Z1, may be employed.

In this example, a configuration, in which the projection magnification of the target light flux that is projected to the examinee's eye E is corrected by changing the size of the target F that is displayed on the display 31, is exemplified and described; however, the configuration is not limited thereto. For example, in this example, the optical length may be changed by moving the optical member based on the set correction amount, and the projection magnification of the target light flux may be corrected. For example, in this case, the optical element provided in the light projecting optical system 30 may be used, or an optical element may be separately provided.

For example, in a case of correcting the projection magnification of the target light flux by using the optical element provided in the light projecting optical system 30, the optical element may be moved in the optical axis direction of the light projecting optical system 30 based on the correction amount set by the controller 70. For example, the projection lens 33 or the projection lens 34 may be moved as the optical element in the direction of the optical axis L2. In addition, for example, the objective lens 14 may be moved as the optical element in the direction of the optical axis L3. For example, when any one of the projection lens or the objective lens is moved in the optical axis direction, the position of the calibration optical system 60 disposed depending on the eye refractive power of the examinee's eye E is changed, and thus it is necessary to move the display 31 in the direction of the optical axis L2. That is, since any one of the projection lens or the objective lens is moved, and thereby the focal point of the target F, which is displayed on the display 31 for the examinee's eye E, deviates, it is necessary to move the display 31 to the focal position. For example, the controller 70 moves any one of the projection lens or the objective lens in the optical axis direction based on the set correction amount and moves the display 31 in the optical axis direction, and thereby the projection magnification of the target light flux may be corrected.

For example, in a case of a configuration in which a plurality of projection lenses or objective lenses are moved in the optical axis direction, it is possible to maintain a focused state of the target that is displayed on the display 31 for the examinee's eye E even when the disposition of the calibration optical system 60 is changed. For example, the controller 70 may correct the projection magnification of the target light flux, by moving the plurality of projection lenses or objective lenses in the optical axis direction, based on the set correction amount.

For example, as described above, the subjective optometry apparatus in this example is capable of controlling the drive portion based on the correction amount and moving the optical element in the optical axis direction of the light projecting optical system. Therefore, the examiner can change the optical length from the display 31 to the examinee's eye E and correct the projection magnification of the target light flux with a simple configuration.

In addition, for example, in the case of correcting the projection magnification of the target light flux by separately providing the optical element, the optical element may be inserted into and removed from the optical axis direction of the light projecting optical system 30 based on the set correction amount. For example, the optical element may be inserted into or removed from any position on the optical axis through which the target light flux that is projected from the display 31 toward the examinee's eye E passes. In other words, the optical element may be inserted into or removed from any position on the optical axis L2 and the optical axis L3. For example, a lens (for example, a convex lens or a concave lens), a prism, a mirror, or the like can be used as such an optical element. In the following description, a case of using the lens as the optical element is exemplified.

For example, in a case of a configuration in which one lens is inserted into or removed from the optical axis L2 or the optical axis L3, one lens is added with respect to the calibration optical system 60 disposed depending on the eye refractive power of the examinee's eye E, and thus the focal point of the target that is displayed on the display 31 for the examinee's eye E is likely to deviate. Therefore, for example, the controller 70 may insert one lens and move the display 31 in the optical axis direction based on the set correction amount, thereby aligning the focal position of the target with the examinee's eye E and correcting the projection magnification of the target light flux.

In addition, for example, in the case of correcting the projection magnification of the target light flux by separately providing the optical element, it is possible to employ a configuration in which the plurality of lenses are inserted into the optical axis L2 and the optical axis L3. At this time, all of the plurality of lenses may be inserted into the optical axis L2 or all may be inserted into the optical axis L3. It is needless to say that any lens of the plurality of lenses may be inserted into the optical axis L2 or any lens may be inserted into the optical axis L3. For example, when the plurality of lenses are inserted, the focal position of the target that is displayed on the display 31 for the examinee's eye E is not changed. For example, the controller 70 may correct the projection magnification of the target light flux, by inserting the plurality of lenses, based on the set correction amount. Convex lenses, concave lenses, or a combination of the convex lenses and the concave lenses may be used as the plurality of lenses.

For example, as described above, the subjective optometry apparatus in this example is capable of controlling the drive portion based on the correction amount and inserting or removing the optical elements into or from the optical path of the light projecting optical system. Therefore, the examiner can change the optical length from the display 31 to the examinee's eye E and correct the projection magnification of the target light flux with a simple configuration.

In this example, a configuration, in which the projection magnification of the target that is projected to the examinee's eye E is corrected in a case where the examinee's eye E deviates from the position Z1 in the Z direction, is exemplified and described, however, the configuration is not limited thereto. For example, a change in projection magnification of the target due to the deviating position of the examinee's eye E from the position Z1 is small, and thus it is not necessary to correct the magnification in some cases. For example, at this time, an allowable range may be set with respect to the deviation of the alignment. For example, such an allowable range may be calculated in advance by performing simulations or experiments. For example, after detecting that the examinee's eye E deviates from the position Z1, the controller 70 determines whether the deviation exceeds the allowable range or is within the allowable range. For example, as described above, the controller 70 may be configured not to correct the projection magnification of the target that is projected to the examinee's eye E when the deviation of the alignment with the examinee's eye E is within the allowable range.

In addition, in this example, a configuration, in which the projection magnification of the target that is projected to the examinee's eye E is corrected in a case where the examinee's eye E slightly moves during the subjective measurement, is exemplified and described; however, the configuration is not limited thereto. For example, a change in projection magnification of the target due to the slightly moving position of the examinee's eye E and the eye refractive power of the examinee's eye E is small, and thus it is not necessary to correct the magnification in some cases. That is, when the slight movement of the examinee's eye E is small and the absolute value of the eye refractive power of the examinee's eye E is small, it is not necessary to correct the projection magnification of the target in some cases. For example, at this time, the allowable range may be set based on the deviation due to the slight movement of the examinee's eye E and the eye refractive power of the examinee's eye E. For example, such an allowable range may be calculated in advance by performing simulations or experiments. For example, the controller 70 determines whether or not the change in projection magnification is within the allowable range when performing the subjective measurement on the examinee's eye E having a low eye refractive power and further measuring the deviation due to the slight movement of the examinee's eye E. For example, the controller 70 may be configured to determine, on the basis of such determination, whether or not the projection magnification of the target that is projected to the examinee's eye E is corrected.

In this example, a case where the examinee's eye E slightly moves during the subjective measurement is exemplified and described; however, the examinee's eye E also significantly moves during the subjective measurement in some cases. For example, in such a case, when the target display of the display 31 is controlled such that the projection magnification of the target light flux is corrected, the magnification exceeds a display range of the display in some cases according to the eye refractive power or the deviation of the examinee's eye E in the Z direction. In other words, a size change of the target F that is displayed on the display 31 cannot correspond to the correction for the projection magnification in some cases. Therefore, when the examinee's eye E significantly moves, the measurement unit 7 may be again aligned with the examinee's eye E, and the pupil conjugate position R may be disposed at the pupil position P of the examinee's eye E. For example, in this case, a configuration in which, even after the alignment with the examinee's eye E is completed, the controller 70 detects the misalignment in the XYZ directions as needed and performs tracking control (tracking) of always measuring the movement of examinee's eye E in the Z direction is employed. For example, as described above, the alignment may be automatically performed along with the movement of the examinee's eye E, and the size of the target F that is displayed on the display 31 may be always corrected.

In this example, the configuration, in which the correction amount for correcting the projection magnification of the target light flux due to the misalignment is acquired by using the correction table, is exemplified and described; however, the example is not limited thereto. For example, when the pupil position P of the examinee's eye E and the pupil conjugate position R are coincident with each other, and the length Δg from the position Z1 to the position Z2 (alignment completion position) is measured, the controller 70 may perform a calculating process of acquiring the correction amount for correcting the projection magnification of the target light flux with the length Δg by using an equation for calculation. For example, the equation for performing the calculating process may be set by performing experiments or simulations in advance or may be stored in the memory 75 provided in the controller 70. For example, as described above, the controller 70 may be configured to acquire the correction amount for correcting the projection magnification of the target light flux according to the misalignment by using the equation.

Similarly, in this example, the configuration, in which the projection magnification of the target light flux is acquired by using the correction table as the examinee's eye E slightly moves, is exemplified and described; however, the configuration is not limited thereto. For example, when the length Δd from the position Z2 (alignment completion position) to the slight moving position S is measured, the controller 70 may perform the calculating process of acquiring the correction amount for correcting the projection magnification of the target light flux with the length Δd and the calibration power of the calibration optical system 60 by using the equation. For example, the equation may be set by performing experiments or simulations in advance or may be stored in the memory 75 provided in the controller 70. For example, as described above, the controller 70 may be configured to set the correction amount for correcting the projection magnification of the target light flux according to the slight movement of the examinee's eye E by using the equation.

In this example, the configuration of acquiring the eye refractive power of the examinee's eye E by the objective measurement optical system provided in the subjective optometry apparatus 1 is exemplified and described; however, the configuration is not limited thereto. For example, a configuration, in which the eye refractive power of the examinee's eye E is acquired by the subjective measurement optical system provided in the subjective optometry apparatus 1, may be employed. In this case, the calibration power of the calibration optical system 60 can be acquired by using the objective eye refractive power (objective value) as described in this example or can be acquired by using the subjective eye refractive power (subjective value) acquired in the subjective measurement. For example, a configuration, in which the subjective value acquired during the subjective measurement is stored in the memory 75 as needed, the examinee's eye E and the controller 70 calls the subjective value when the examinee's eye E slightly moves from the alignment completion position, may be employed.

In addition, in this example, the configuration of acquiring the eye refractive power of the examinee's eye E by the objective measurement optical system provided in the subjective optometry apparatus 1 is exemplified and described; however, the configuration is not limited thereto. For example, the eye refractive power of the examinee's eye E may be acquired by using an objective value or a subjective value of the examinee's eye E acquired by another apparatus. For example, in this case, a configuration, in which the subjective optometry apparatus 1 includes a receiving function for receiving the eye refractive power from the other apparatus, may be employed. In addition, for example, in this case, a configuration in which the examiner inputs the eye refractive power of the examinee's eye E may be employed.

In this example, the subjective optometry apparatus 1 including the optical system in which the concave mirror 85 is disposed as the fixed optical element is described; however, the apparatus is not limited thereto. For example, the subjective optometry apparatus 1 in this example may be provided with the optical system in which the concave mirror 85 is not provided but a convex lens is fixedly disposed. For example, since the projection magnification of the target light flux changes even in the optical system in which the convex lens is fixedly disposed, it is possible to correct the projection magnification in the same manner as that in this example.

In this example, a configuration, in which the operation length of the examinee's eye E (alignment state) is measured, and thereby the length from the examinee's eye E to the pupil conjugate position R of the light projecting optical system 30 is measured, is exemplified and described; however, the example is not limited thereto. For example, the length from the examinee's eye E to the pupil conjugate position R may be obtained by detecting the pupil position P of the examinee's eye E. For example, in this case, the subjective optometry apparatus 1 may be provided with an imaging optical system for imaging a sectional image of the examinee's eye E In this manner, a configuration, in which the pupil position P is directly detected from the sectional image of the examinee's eye E, and a length from the examinee's eye E to the pupil conjugate position R of the light projecting optical system 30 is obtained, may be employed.

In this example, the alignment with the examinee's eye E in the operation length direction (Z direction) is described; however, in a case where the examinee's eye E deviates from the position Z1 in the X direction and the Y direction, the alignment in the X direction and the Y direction may be adjusted. For example, in this example, the deflecting mirror 81 and the measurement unit 7 are integrally moved in the X direction, and thereby it is possible to perform the alignment of the examinee's eye E in the X direction (rightward-leftward direction). In addition, for example, in this example, the deflecting mirror 81 and the measurement unit 7 are integrally moved in the Z direction, and thereby it is possible to perform the alignment of the examinee's eye E in the Y direction (upward-downward direction).

In addition, for example, in a case where the examinee's eye E slightly moves from the alignment completion position (for example, the position Z2) in the X direction and the Y direction, a configuration, in which the size h of the target F is changed in consideration of the projection magnification of the target light flux in the X direction and the Y direction, may be employed.

In this example, a configuration, in which the deflecting mirror 81 and the measurement unit 7 are integrally driven, and thereby the alignment in the XYZ directions is adjusted, is exemplified and described; however, the configuration is not limited thereto. For example, in this example, a configuration, in which the drive of the deflecting mirror 81 and the measurement unit 7 enables the positional relationship between the examinee's eye E and the subjective measurement portion and the objective measurement portion to be adjusted, may be employed. That is, a configuration, in which it is possible to perform adjustment in the XYZ directions such that the target light flux from the light projecting optical system 30 is formed on the fundus of the examinee's eye E. For example, in this case, a configuration, in which the subjective optometry apparatus 1 is movable in the XYZ directions with respect to the chin rest 5, may be employed such that a configuration of moving the subjective optometry apparatus 1 may be employed. In addition, for example, a configuration, in which the deflecting mirror 81 is fixedly disposed, and only the measurement unit 7 moves, may be employed. In addition, for example, a configuration in which it is possible to perform the adjustment in the XYZ directions by using only the deflecting mirror 81, may be employed. In this case, for example, a configuration, in which the deflecting mirror 81 is rotatably driven and moves in the Z direction, and thereby the length between the deflecting mirror 81 and the measurement unit 7 changes, is employed.

Although not described in this example, in a case where the eye of the examinee rotates on a plane in the horizontal direction (plane in the X direction), and the positions of the examinee's left eye EL and the examinee's right eye ER are different from each other in the frontward-rearward direction (Z direction), the control operation described above may be performed on the examinee's right and left eyes E. In this manner, for example, the correction for the projection magnifications of the target is performed for both of the examinee's left eye EL and the examinee's right eye ER, and thus it is possible to project the targets having the same size toward the examinee's right and left eyes E. Therefore, even in a case of examining vision functions of both of the examinee's eyes E or the like, the examiner can obtain the measurement result with accuracy.

What is claimed is:

1. A subjective optometry apparatus that subjectively measures optical characteristics of an examinee's eye, the subjective optometry apparatus comprising:
    a light projecting optical system that projects a target light flux to the examinee's eye;
    a fixed optical element that guides an image of the target light flux to the examinee's eye so as to have an optically predetermined examination length;
    a calibration optical system disposed in an optical path of the light projecting optical system to change the optical characteristics of the examinee's eye;
    a measurement unit that accommodates the light projecting optical system;
    a positional information acquiring portion that acquires positional information of the measurement unit;
    a correction amount setting portion that sets a correction amount for correcting a projection magnification of the target light flux projected to the examinee's eye, based on the positional information; and
    a correction portion that corrects the projection magnification of the target light flux based on the correction amount set by the correction amount setting portion.

2. The subjective optometry apparatus according to claim 1, further comprising:
    a detection portion that detects a length between the examinee's eye and a pupil conjugate position of the light projecting optical system; and
    an adjustment portion that adjusts a position of the measurement unit in an optical axis direction based on a detection result by the detection portion.

3. The subjective optometry apparatus according to claim 1,
    wherein the light projecting optical system has a display, and the target light flux is emitted by displaying a target on the display, and
    wherein the correction portion changes a size of the target displayed on the display, based on the correction amount, to correct the projection magnification of the target light flux.

4. The subjective optometry apparatus according to claim 1, further comprising:
    an optical element that is movable with respect to the optical path of the light projecting optical system; and
    a drive portion that moves the optical element with respect to the optical path of the light projecting optical system,
    wherein the correction portion controls the drive portion such that the optical element is moved, based on the correction amount, to correct the projection magnification of the target light flux.

5. The subjective optometry apparatus according to claim 4,
    wherein the correction portion controls the drive portion such that the optical element is moved in an optical axis direction of the light projecting optical system, based on the correction amount, to correct the projection magnification of the target light flux.

6. The subjective optometry apparatus according to claim 4,
    wherein the correction portion controls the drive portion such that the optical element is inserted into or is removed from the optical path of the light projecting optical system, based on the correction amount, to correct the projection magnification of the target light flux.

7. The subjective optometry apparatus according to claim 1,
    wherein the fixed optical element is a concave mirror.

8. The subjective optometry apparatus according to claim 1,
    wherein the fixed optical element guides the target light flux calibrated by the calibration optical system to the examinee's eye.

9. A storage medium that stores a subjective optometry program used in a subjective optometry apparatus that subjectively measures optical characteristics of an examinee's eye and includes a light projecting optical system that projects a target light flux to the examinee's eye, a fixed optical element that guides an image of the target light flux to the examinee's eye so as to have an optically predetermined examination length, and a calibration optical system disposed in an optical path of the light projecting optical system to change the optical characteristics of the examinee's eye,
    the subjective optometry program, when executed by a processor of the subjective optometry apparatus, causing the subjective optometry apparatus to execute:
    a positional information acquiring step of acquiring positional information of the measurement unit that accommodates the light projecting optical system;
    a correction amount setting step of setting a correction amount for correcting a projection magnification of the target light flux projected to the examinee's eye, based on the positional information; and
    a correcting step of correcting the projection magnification of the target light flux based on the correction amount set in the correction amount setting step.

* * * * *